(12) United States Patent
Kaula et al.

(10) Patent No.: US 9,594,877 B2
(45) Date of Patent: Mar. 14, 2017

(54) VIRTUAL REALITY REPRESENTATION OF MEDICAL DEVICES

(75) Inventors: Norbert Kaula, Arvada, CO (US); Yohannes Iyassu, Denver, CO (US)

(73) Assignee: Nuvectra Corporation, Plano, TX (US)

( * ) Notice: Subject to any disclaimer, the term of this patent is extended or adjusted under 35 U.S.C. 154(b) by 837 days.

(21) Appl. No.: 13/601,449

(22) Filed: Aug. 31, 2012

(65) Prior Publication Data

US 2014/0062900 A1    Mar. 6, 2014

(51) Int. Cl.
*G06F 3/00* (2006.01)
*G06F 9/00* (2006.01)
(Continued)

(52) U.S. Cl.
CPC ..... *G06F 19/3437* (2013.01); *A61N 1/37247* (2013.01)

(58) Field of Classification Search
CPC ........ G06F 9/4443; G06F 8/34; G06F 3/0486; G06F 8/38; G06F 3/0481; G06F 3/0482; G06F 3/04812; G06F 3/04847; G06F 19/3437; G06Q 10/10; H04N 1/00389; H04N 1/00411; A61N 1/37247
See application file for complete search history.

(56) References Cited

U.S. PATENT DOCUMENTS

| | | |
|---|---|---|
| 4,432,360 A | 2/1984 | Mumford et al. |
| 4,964,407 A * | 10/1990 | Baker, Jr. ............. A61N 1/3706 607/27 |

(Continued)

FOREIGN PATENT DOCUMENTS

| | | |
|---|---|---|
| EP | 1192972 | 4/2002 |
| EP | 2277586 | 1/2011 |

(Continued)

OTHER PUBLICATIONS

Synalink Features, SynaMed Web Page, http://synamed.com/synalinkFeatures.html., Copyright 2010, 2 pgs.
(Continued)

*Primary Examiner* — Kieu Vu
*Assistant Examiner* — Anita D Chaudhuri
(74) *Attorney, Agent, or Firm* — Haynes and Boone, LLP; Eric Li

(57) ABSTRACT

The present disclosure involves a method of facilitating visualization in a medical context. The method includes displaying a virtual reality representation of a medical device via a touch-sensitive user interface. The virtual reality representation of the medical device includes a movable and rotatable three-dimensional model of the medical device. The method includes displaying a virtual reality representation of an anatomical environment of a patient via a touch-sensitive user interface. The virtual reality representation of the anatomical environment is zoomable and scalable. The method includes customizing the virtual reality representation of the medical device. The method includes positioning the customized virtual reality representation of the medical device in an appropriate location of the virtual reality representation of the anatomical environment. The customizing and the positioning are performed in response to user input.

40 Claims, 19 Drawing Sheets

(51) Int. Cl.
  *G06F 17/00* (2006.01)
  *G06F 19/00* (2011.01)
  *A61N 1/372* (2006.01)

(56) References Cited

U.S. PATENT DOCUMENTS

| | | | |
|---|---|---|---|
| 5,286,202 A | 2/1994 | De Gyarfas et al. | |
| 5,304,206 A | 4/1994 | Baker, Jr. et al. | |
| 5,312,446 A | 5/1994 | Holschbach et al. | |
| 5,370,672 A | 12/1994 | Fowler et al. | |
| 5,383,914 A | 1/1995 | O'Phelan | |
| 5,421,830 A | 6/1995 | Epstein et al. | |
| 5,628,776 A | 5/1997 | Paul et al. | |
| 5,713,937 A | 2/1998 | Nappholz et al. | |
| 5,722,999 A | 3/1998 | Snell | |
| 5,724,996 A | 3/1998 | Piunti | |
| 5,819,740 A | 10/1998 | Muhlenberg | |
| 5,879,374 A | 3/1999 | Powers et al. | |
| 5,905,500 A | 5/1999 | Kamen et al. | |
| 5,938,690 A | 8/1999 | Law et al. | |
| 6,016,447 A | 1/2000 | Juran et al. | |
| 6,016,448 A | 1/2000 | Busacker et al. | |
| 6,052,624 A | 4/2000 | Mann | |
| 6,083,156 A | 7/2000 | Lisiecki | |
| 6,148,233 A | 11/2000 | Owen et al. | |
| 6,154,675 A | 11/2000 | Juran et al. | |
| 6,216,036 B1 | 4/2001 | Jenkins et al. | |
| 6,246,414 B1 | 6/2001 | Kawasaki | |
| 6,249,705 B1 | 6/2001 | Snell | |
| 6,278,890 B1 | 8/2001 | Chassaing et al. | |
| 6,307,554 B1 | 10/2001 | Arai et al. | |
| 6,308,102 B1 | 10/2001 | Sieracki et al. | |
| 6,345,200 B1 | 2/2002 | Mouchawar et al. | |
| 6,386,882 B1 | 5/2002 | Linberg | |
| 6,442,432 B2 | 8/2002 | Lee | |
| 6,516,227 B1* | 2/2003 | Meadows et al. | 607/46 |
| 6,525,727 B1 | 2/2003 | Junkins et al. | |
| 6,564,104 B2 | 5/2003 | Nelson et al. | |
| 6,587,104 B1 | 7/2003 | Hoppe | |
| 6,611,267 B2 | 8/2003 | Migdal et al. | |
| 6,622,048 B1 | 9/2003 | Mann et al. | |
| 6,669,631 B2 | 12/2003 | Norris et al. | |
| 6,786,405 B2 | 9/2004 | Weidenhoefer | |
| 6,852,080 B2 | 2/2005 | Bardy | |
| 6,882,982 B2 | 4/2005 | McMenimen et al. | |
| 6,895,280 B2 | 5/2005 | Meadows et al. | |
| 6,920,360 B2 | 7/2005 | Lee et al. | |
| 6,931,155 B1 | 8/2005 | Gioia | |
| 6,961,448 B2 | 11/2005 | Nichols et al. | |
| 6,961,617 B1 | 11/2005 | Snell | |
| 7,003,349 B1 | 2/2006 | Andersson et al. | |
| 7,034,823 B2 | 4/2006 | Dunnet | |
| 7,058,453 B2 | 6/2006 | Nelson et al. | |
| 7,060,030 B2 | 6/2006 | Von Arx et al. | |
| 7,065,409 B2 | 6/2006 | Mazar | |
| 7,066,910 B2 | 6/2006 | Bauhahn et al. | |
| 7,076,303 B2 | 7/2006 | Linberg | |
| 7,087,015 B1 | 8/2006 | Comrie et al. | |
| 7,092,761 B1 | 8/2006 | Cappa et al. | |
| 7,107,102 B2 | 9/2006 | Daignault et al. | |
| 7,142,923 B2 | 11/2006 | North et al. | |
| 7,181,286 B2 | 2/2007 | Sieracki et al. | |
| 7,181,505 B2 | 2/2007 | Haller et al. | |
| 7,184,837 B2 | 2/2007 | Goetz | |
| 7,239,926 B2 | 7/2007 | Goetz | |
| 7,266,412 B2 | 9/2007 | Stypulkowski | |
| 7,299,085 B2 | 11/2007 | Bergelson et al. | |
| 7,359,751 B1 | 4/2008 | Erickson et al. | |
| 7,373,204 B2 | 5/2008 | Gelfand et al. | |
| 7,440,806 B1 | 10/2008 | Whitehurst et al. | |
| 7,452,336 B2 | 11/2008 | Thompson | |
| 7,463,927 B1 | 12/2008 | Chaouat | |
| 7,474,223 B2 | 1/2009 | Nycz et al. | |
| 7,481,759 B2 | 1/2009 | Whitehurst et al. | |
| 7,489,970 B2 | 2/2009 | Lee et al. | |
| 7,496,403 B2 | 2/2009 | Cao et al. | |
| 7,499,048 B2 | 3/2009 | Sieracki et al. | |
| 7,505,815 B2 | 3/2009 | Lee et al. | |
| 7,551,960 B2 | 6/2009 | Forsberg et al. | |
| 7,602,384 B2 | 10/2009 | Rosenberg et al. | |
| 7,617,002 B2 | 11/2009 | Goetz | |
| 7,627,372 B2 | 12/2009 | Vaisnys et al. | |
| 7,640,059 B2 | 12/2009 | Forsberg et al. | |
| 7,657,317 B2 | 2/2010 | Thacker et al. | |
| 7,685,005 B2 | 3/2010 | Riff et al. | |
| 7,711,603 B2 | 5/2010 | Vanker et al. | |
| 7,720,549 B2 | 5/2010 | Schroeppel et al. | |
| 7,747,330 B2 | 6/2010 | Nolan et al. | |
| 7,774,067 B2 | 8/2010 | Keacher et al. | |
| 7,778,710 B2 | 8/2010 | Propato | |
| 7,801,596 B2 | 9/2010 | Fischell et al. | |
| 7,801,611 B2 | 9/2010 | Persen et al. | |
| 7,805,199 B2 | 9/2010 | KenKnight et al. | |
| 7,822,483 B2 | 10/2010 | Stone et al. | |
| 7,853,323 B2 | 12/2010 | Goetz | |
| 7,885,712 B2 | 2/2011 | Goetz et al. | |
| 7,890,180 B2 | 2/2011 | Quiles et al. | |
| 7,928,995 B2 | 4/2011 | Daignault | |
| 7,934,508 B2 | 5/2011 | Behm | |
| 7,940,933 B2 | 5/2011 | Corndorf | |
| 7,953,492 B2 | 5/2011 | Corndorf | |
| 7,953,612 B1 | 5/2011 | Palmese et al. | |
| 7,957,808 B2 | 6/2011 | Dawant et al. | |
| 7,978,062 B2 | 7/2011 | LaLonde et al. | |
| 7,991,482 B2 | 8/2011 | Bradley | |
| 8,014,863 B2 | 9/2011 | Zhang et al. | |
| 8,021,298 B2 | 9/2011 | Barid et al. | |
| 8,027,726 B2 | 9/2011 | Ternes | |
| 8,046,241 B1 | 10/2011 | Dodson | |
| 8,060,216 B2 | 11/2011 | Greenberg et al. | |
| 8,068,915 B2 | 11/2011 | Lee et al. | |
| 8,068,918 B2 | 11/2011 | Vallapureddy et al. | |
| 8,078,440 B2 | 12/2011 | Otto et al. | |
| 8,082,162 B2 | 12/2011 | Flood | |
| 8,121,702 B2 | 2/2012 | King | |
| 8,135,566 B2 | 3/2012 | Marshall et al. | |
| 8,140,160 B2 | 3/2012 | Pless et al. | |
| 8,140,167 B2 | 3/2012 | Donders et al. | |
| 8,160,328 B2 | 4/2012 | Goetz et al. | |
| 8,160,704 B2 | 4/2012 | Freeberg | |
| 8,165,385 B2 | 4/2012 | Reeves et al. | |
| 8,187,015 B2 | 5/2012 | Boyd et al. | |
| 8,200,324 B2 | 6/2012 | Shen et al. | |
| 8,200,340 B2 | 6/2012 | Skelton et al. | |
| 8,219,206 B2 | 7/2012 | Skelton et al. | |
| 8,233,991 B2 | 7/2012 | Woods et al. | |
| 8,246,680 B2 | 8/2012 | Betz et al. | |
| 8,249,713 B2 | 8/2012 | Fang et al. | |
| 8,255,060 B2 | 8/2012 | Goetz et al. | |
| 8,323,218 B2 | 12/2012 | Davis et al. | |
| 8,326,433 B2 | 12/2012 | Blum et al. | |
| 8,340,775 B1 | 12/2012 | Cullen et al. | |
| 8,382,666 B1 | 2/2013 | Mao et al. | |
| 8,386,032 B2 | 2/2013 | Bachinski et al. | |
| 8,401,666 B2 | 3/2013 | Skelton et al. | |
| 8,428,727 B2 | 4/2013 | Bolea et al. | |
| 2001/0037220 A1 | 11/2001 | Merry et al. | |
| 2003/0076301 A1 | 4/2003 | Tsuk et al. | |
| 2003/0107572 A1 | 6/2003 | Smith et al. | |
| 2003/0139652 A1 | 7/2003 | Kang et al. | |
| 2003/0171911 A1 | 9/2003 | Fairweather | |
| 2003/0177031 A1 | 9/2003 | Malek | |
| 2004/0088374 A1 | 5/2004 | Webb et al. | |
| 2004/0122477 A1 | 6/2004 | Whitehurst et al. | |
| 2004/0210273 A1 | 10/2004 | Wang | |
| 2005/0107831 A1 | 5/2005 | Hill et al. | |
| 2005/0149356 A1 | 7/2005 | Cyr et al. | |
| 2005/0168460 A1 | 8/2005 | Razdan et al. | |
| 2005/0277872 A1 | 12/2005 | Colby et al. | |
| 2006/0048076 A1* | 3/2006 | Vronay et al. | 715/850 |
| 2006/0073455 A1* | 4/2006 | Buyl et al. | 434/262 |
| 2006/0089888 A1 | 4/2006 | Roger | |
| 2006/0100832 A1 | 5/2006 | Bowman | |
| 2006/0114516 A1* | 6/2006 | Rothschild | 358/3.28 |

(56) References Cited

U.S. PATENT DOCUMENTS

| | | |
|---|---|---|
| 2006/0241720 A1 | 10/2006 | Woods et al. |
| 2006/0242159 A1 | 10/2006 | Bishop et al. |
| 2006/0282168 A1 | 12/2006 | Sherman et al. |
| 2007/0078497 A1 | 4/2007 | Vandanacker |
| 2007/0093998 A1 | 4/2007 | El-Baroudi et al. |
| 2007/0179349 A1 | 8/2007 | Hoyme et al. |
| 2007/0203537 A1 | 8/2007 | Goetz et al. |
| 2007/0203538 A1 | 8/2007 | Stone et al. |
| 2007/0203543 A1 | 8/2007 | Stone et al. |
| 2007/0213790 A1 | 9/2007 | Nolan et al. |
| 2008/0004675 A1 | 1/2008 | King et al. |
| 2008/0033303 A1 | 2/2008 | Wariar et al. |
| 2008/0046036 A1 | 2/2008 | King et al. |
| 2008/0140161 A1 | 6/2008 | Goetz et al. |
| 2008/0177362 A1 | 7/2008 | Phillips et al. |
| 2008/0218517 A1 | 9/2008 | Holmdahl |
| 2008/0262565 A1 | 10/2008 | Bentwich |
| 2009/0018617 A1 | 1/2009 | Skelton et al. |
| 2009/0018619 A1 | 1/2009 | Skelton et al. |
| 2009/0024178 A1 | 1/2009 | Hennig |
| 2009/0048871 A1 | 2/2009 | Skomra |
| 2009/0089034 A1 | 4/2009 | Penney et al. |
| 2009/0099624 A1 | 4/2009 | Kokones et al. |
| 2009/0132009 A1 | 5/2009 | Torgenson et al. |
| 2009/0136094 A1 | 5/2009 | Driver et al. |
| 2009/0149977 A1* | 6/2009 | Schendel .................. 700/98 |
| 2009/0196471 A1 | 8/2009 | Goetz et al. |
| 2009/0234873 A1 | 9/2009 | Li et al. |
| 2009/0264967 A1 | 10/2009 | Giftakis et al. |
| 2009/0281596 A1 | 11/2009 | King et al. |
| 2010/0004033 A1 | 1/2010 | Choe et al. |
| 2010/0010566 A1 | 1/2010 | Thacker et al. |
| 2010/0010574 A1 | 1/2010 | Skelton et al. |
| 2010/0010580 A1 | 1/2010 | Skelton et al. |
| 2010/0058462 A1 | 3/2010 | Chow |
| 2010/0076534 A1 | 3/2010 | Mock |
| 2010/0090004 A1 | 4/2010 | Sands et al. |
| 2010/0106475 A1 | 4/2010 | Smith et al. |
| 2010/0123547 A1 | 5/2010 | Stevenson et al. |
| 2010/0152534 A1 | 6/2010 | Kim et al. |
| 2010/0161345 A1 | 6/2010 | Cain et al. |
| 2010/0198103 A1 | 8/2010 | Meadows et al. |
| 2010/0198304 A1 | 8/2010 | Wang |
| 2010/0222845 A1 | 9/2010 | Goetz |
| 2010/0223020 A1 | 9/2010 | Goetz |
| 2010/0265072 A1 | 10/2010 | Goetz et al. |
| 2010/0268304 A1 | 10/2010 | Matos |
| 2010/0280578 A1 | 11/2010 | Skelton et al. |
| 2011/0004059 A1 | 1/2011 | Arneson et al. |
| 2011/0015514 A1 | 1/2011 | Skalli et al. |
| 2011/0015693 A1 | 1/2011 | Williamson |
| 2011/0023343 A1 | 2/2011 | Turner et al. |
| 2011/0038498 A1 | 2/2011 | Edgar |
| 2011/0040546 A1 | 2/2011 | Gerber et al. |
| 2011/0040547 A1 | 2/2011 | Gerber et al. |
| 2011/0046697 A1 | 2/2011 | Gerber et al. |
| 2011/0054560 A1 | 3/2011 | Rosenberg et al. |
| 2011/0054870 A1 | 3/2011 | Dariush et al. |
| 2011/0077459 A1 | 3/2011 | Rofougaran |
| 2011/0077616 A1 | 3/2011 | Bennet et al. |
| 2011/0093030 A1 | 4/2011 | Goetz et al. |
| 2011/0093047 A1 | 4/2011 | Davis et al. |
| 2011/0093051 A1 | 4/2011 | Davis et al. |
| 2011/0153341 A1 | 6/2011 | Diaz-Cortes |
| 2011/0170739 A1 | 7/2011 | Gillam et al. |
| 2011/0172564 A1 | 7/2011 | Drew |
| 2011/0172737 A1 | 7/2011 | Davis et al. |
| 2011/0172744 A1 | 7/2011 | Davis et al. |
| 2011/0185178 A1 | 7/2011 | Gotthardt |
| 2011/0191275 A1 | 8/2011 | Lujan et al. |
| 2011/0224523 A1 | 9/2011 | Burdiman |
| 2011/0246219 A1 | 10/2011 | Smith et al. |
| 2011/0264165 A1 | 10/2011 | Molnar et al. |
| 2011/0270358 A1 | 11/2011 | Davis et al. |
| 2011/0282414 A1 | 11/2011 | Kothandaraman et al. |
| 2011/0305376 A1 | 12/2011 | Neff |
| 2011/0307284 A1 | 12/2011 | Thompson et al. |
| 2011/0313268 A1 | 12/2011 | Kokones et al. |
| 2011/0313487 A1 | 12/2011 | Kokones et al. |
| 2012/0041518 A1 | 2/2012 | Kim et al. |
| 2012/0046715 A1 | 2/2012 | Moffitt et al. |
| 2012/0071947 A1 | 3/2012 | Gupta et al. |
| 2012/0083857 A1 | 4/2012 | Bradley et al. |
| 2012/0084689 A1 | 4/2012 | Ledet et al. |
| 2012/0089008 A1 | 4/2012 | Strehl et al. |
| 2012/0109230 A1 | 5/2012 | Kothandaraman et al. |
| 2012/0192874 A1 | 8/2012 | Bolea et al. |
| 2012/0239116 A1 | 9/2012 | Lee et al. |
| 2012/0256857 A1 | 10/2012 | Mak |
| 2012/0265269 A1 | 10/2012 | Lui et al. |
| 2012/0277828 A1 | 11/2012 | O'Conner et al. |
| 2012/0290041 A1 | 11/2012 | Kim et al. |
| 2012/0290272 A1 | 11/2012 | Bryan |
| 2012/0290976 A1 | 11/2012 | Lahm et al. |
| 2012/0296392 A1 | 11/2012 | Lee et al. |
| 2012/0296396 A1 | 11/2012 | Moffitt et al. |
| 2012/0296397 A1 | 11/2012 | Vansickle |
| 2012/0303087 A1 | 11/2012 | Moffitt et al. |
| 2012/0310300 A1 | 12/2012 | Kaula et al. |
| 2013/0023950 A1 | 1/2013 | Gauthier |
| 2013/0060299 A1 | 3/2013 | Polefko et al. |
| 2013/0060300 A1 | 3/2013 | Polefko et al. |
| 2013/0060301 A1 | 3/2013 | Polefko et al. |
| 2013/0060302 A1 | 3/2013 | Polefko et al. |
| 2013/0079848 A1 | 3/2013 | Campbell et al. |

FOREIGN PATENT DOCUMENTS

| | | |
|---|---|---|
| WO | WO 9959106 | 11/1999 |
| WO | WO 0209808 | 2/2002 |
| WO | WO 02084637 | 10/2002 |
| WO | WO 2009113102 | 9/2009 |
| WO | WO 2011028261 | 3/2011 |
| WO | WO 2011063248 | 5/2011 |
| WO | WO 2011104028 | 9/2011 |
| WO | WO 2011123669 | 10/2011 |
| WO | WO 2012018851 | 2/2012 |
| WO | WO 2012021862 | 2/2012 |
| WO | WO 2012135949 | 10/2012 |
| WO | WO 2013023085 | 2/2013 |

OTHER PUBLICATIONS

Boston Scientific Corporation, "Boston Scientific Precision Spectra System Programming Manual", Copyright 2010, 580 pgs.

* cited by examiner

VIRTUAL REALITY REPRESENTATION OF MEDICAL DEVICES

BACKGROUND

As medical device technologies continue to evolve, active implanted medical devices have gained increasing popularity in the medical field. For example, one type of implanted medical device includes neurostimulator devices, which are battery-powered or battery-less devices that are designed to deliver electrical stimulation to a patient. Through proper electrical stimulation, the neurostimulator devices can provide pain relief for patients.

An implanted medical device (for example a neurostimulator) can be controlled using an electronic programming device such as a clinician programmer or a patient programmer. These programmers can be used by medical personnel or the patient to define the particular electrical stimulation therapy to be delivered to a target area of the patient's body or alter one or more parameters of the electrical stimulation therapy. Advances in the medical device field have improved these electronic programmers. However, existing electronic programmers may still have shortcomings such as inadequate representation or visualization of medical devices. For example, existing electronic programmers may not allow a user to visualize the actual look of the stimulation implanted lead or the location or orientation of an implantable medical device within the appropriate anatomical surroundings of a patient.

Therefore, although electronic programming devices for controlling implanted medical devices have been generally adequate for their intended purposes, they have not been entirely satisfactory in every aspect.

SUMMARY

One of the broader forms of the present disclosure involves electronic device configured to visualize one or more medical devices in its suitable anatomical surrounding. The electronic device includes: a touchscreen display configured to receive input from a user and display an output to the user; a memory storage component configured to store programming code; and a computer processor configured to execute the programming code to perform the following tasks: illustrating, via the touchscreen display, a three-dimensional (3-D) model of a medical device, wherein the 3-D model is configured to be moved and rotated in response to user input; illustrating, via the touchscreen display, a visual representation of a suitable anatomical surrounding for the medical device, wherein the visual representation of the anatomical surrounding is configured to be zoomed in and out and scaled up and down in response to user input; choosing, in response to user input, a configuration for the 3-D model of the medical device; and placing, in response to user input, the 3-D model of the medical device in a target position of the visual representation of the anatomical surrounding.

Another one of the broader forms of the present disclosure involves a medical system. The medical system includes: one or more medical devices configurable to deliver a medical therapy to a patient; and an electronic device configured to provide a visual representation of the one or more medical devices via a touch-sensitive visual user interface, wherein the electronic device includes a non-transitory, tangible machine-readable storage medium storing a computer application, wherein the computer application contains machine-readable instructions that when executed electronically by processors, perform the following actions: demonstrating, via the touch-sensitive visual user interface, virtual reality representations of first and second medical devices, the first and second medical devices each being a respective one of the one or more medical devices; demonstrating, via the touch-sensitive visual user interface, a virtual reality representation of a suitable anatomical environment for at least one of the first and second medical devices; positioning the at least one of the first and second medical devices in a target area of the anatomical environment; and simulating an interaction between the first and second medical devices in response to user input.

Yet another one of the broader forms of the present disclosure involves a method of facilitating visualization of devices in a medical context. The method includes: displaying, via a touch-sensitive user interface, a virtual reality representation of a medical device, wherein the virtual reality representation of the medical device includes a movable and rotatable three-dimensional model of the medical device; displaying, via the touch-sensitive user interface, a virtual reality representation of an anatomical environment of a patient, wherein the virtual reality representation of the anatomical environment is zoomable and scalable; customizing the virtual reality representation of the medical device; and positioning the customized virtual reality representation of the medical device in an target location of the virtual reality representation of the anatomical environment; wherein the customizing and the positioning are performed in response to user input.

One more of the broader forms of the present disclosure involves an electronic apparatus for displaying virtual reality representations of medical devices. The electronic apparatus includes: user interface means for communicating with a user, the user interface means including a touch-sensitive screen; memory storage means for storing executable instructions; and computer processor means for executing the instructions to perform: displaying, via the touch-sensitive screen, a virtual representation of a portion of a human body; displaying, via the touch-sensitive screen, a virtual carousel containing a plurality of three-dimensional (3-D) models corresponding to a plurality of different types of medical devices, respectively; and placing, in response to user input received through the user interface means, the 3-D models of one or more of the medical devices within an appropriate location of the virtual representation of the portion of the human body.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In the figures, elements having the same designation have the same or similar functions.

DETAILED DESCRIPTION

Figure 1:
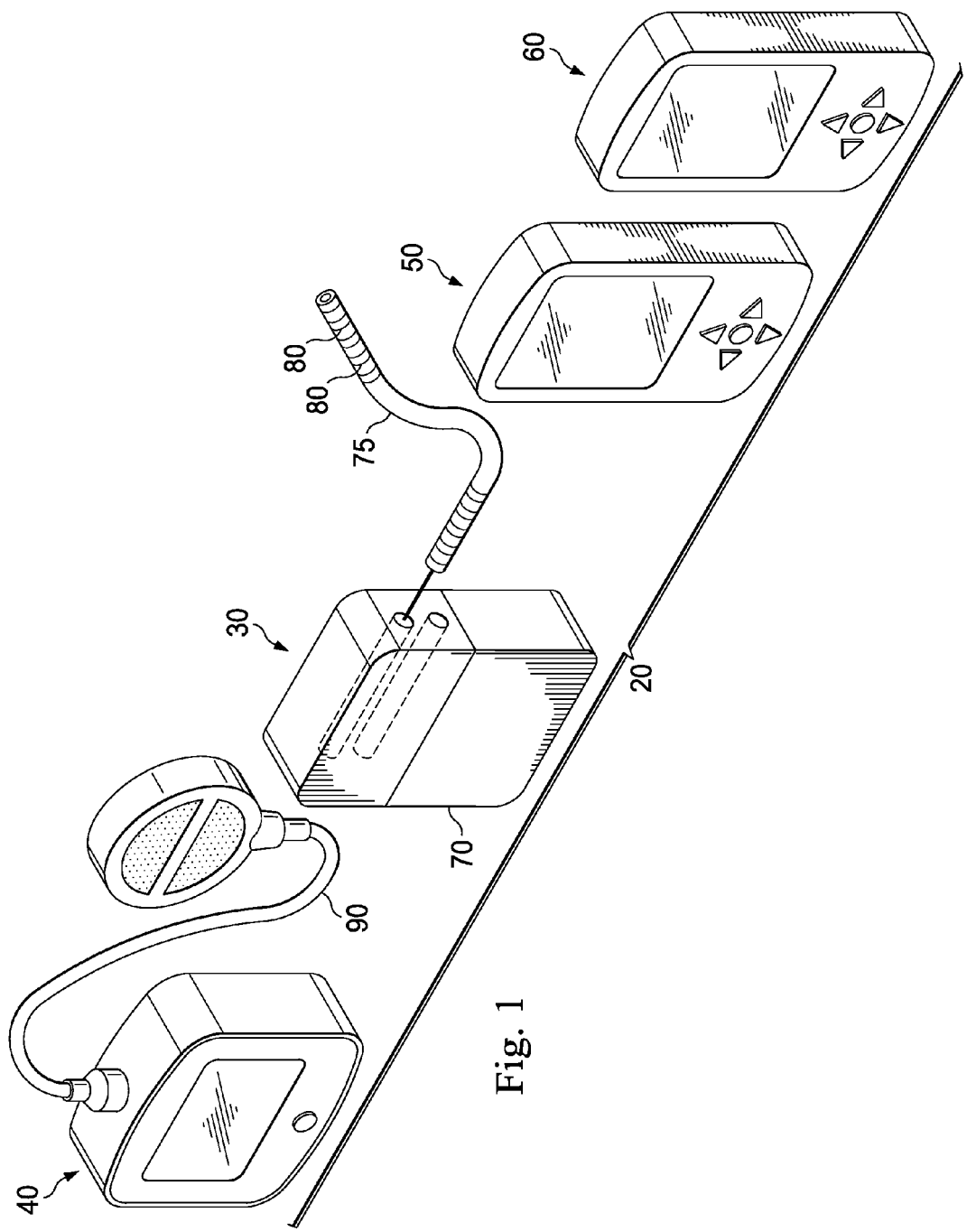
FIG. 1 is a simplified block diagram of a medical system according to various aspects of the present disclosure.

It is to be understood that the following disclosure provides many different embodiments, or examples, for implementing different features of the invention. Specific examples of components and arrangements are described below to simplify the present disclosure. These are, of course, merely examples and are not intended to be limiting. Various features may be arbitrarily drawn in different scales for simplicity and clarity.

Electronic programmers have been used to configure or program active implanted medical devices such as neurostimulators so that they can be operated in a certain manner. These electronic programmers include clinician programmers and patient programmers, each of which may be a handheld device. A clinician programmer allows a medical professional (e.g., a doctor or a nurse) to define the particular electrical stimulation therapy to be delivered to a target area of the patient's body, while a patient programmer allows a patient to alter one or more parameters of the electrical stimulation therapy.

Over the years, these electronic programmers have achieved significant improvements, for example, improvements in size, power consumption, lifetime, and ease of use. However, existing programmers in the medical field may still have drawbacks. One such drawback of existing programmers is their inability to provide adequate visual representation of medical devices, such as an accurate virtual reality representation. In more detail, virtual reality involves using three-dimensional (3-D) models to portray objects in space. Existing programmers have not fully integrated the capabilities of virtual reality with respect to the representation of medical devices. In some cases, existing programmers represent medical devices with a two-dimensional (2-D) model, which cannot accurately portray how the medical device is located or oriented.

To the extent that some existing programmers may offer rudimentary some 3-D representation of medical devices, such representation may still be limited in many respects. As one example, existing 3-D representations of medical devices may not be customizable either with respect to the medical device itself or with respect to the patient. As another example, existing 3-D representations of medical devices lack precision in their visualization of the medical device, for instance precision in the connections and anatomical surroundings of the medical device. As yet another example, existing 3-D representations of medical devices are incapable of detecting and communicating potential problems with the proposed implant(s). For example, the representation may not be able to indicate if connections from one medical device (e.g., a lead) to another (e.g., a pulse generator) are incorrect. Consequently, a user of the programmer is not timely alerted to the potential problems with the proposed set up of the medical devices.

To overcome these problems associated with existing electronic programmers, a user interface having an advanced virtual reality representation of medical devices is implemented on an electronic programmer according to various aspects of the present disclosure.

Referring to FIG. 1, a simplified block diagram of an implanted medical device system 20 is illustrated to provide an example context of the various aspects of the present disclosure. The implanted medical system 20 includes an implantable medical device 30, an external charger 40, a patient programmer 50, and a clinician programmer 60. The implantable medical device 30 can be implanted in a patient's body tissue. In the illustrated embodiment, the implantable medical device 30 includes an implanted pulse generator (IPG) 70 that is coupled to one end of an implanted lead 75. The other end of the implanted lead 75 includes multiple electrode surfaces 80 through which electrical current is applied to a desired part of a body tissue of a patient. The implanted lead 75 incorporates electrical conductors to provide a path for that current to travel to the body tissue from the IPG 70. Although only one implanted lead 75 is shown in FIG. 1, it is understood that a plurality of implanted leads may be attached to the IPG 70.

Although an IPG is used here as an example, it is understood that the various aspects of the present disclosure apply to an external pulse generator (EPG) as well. An EPG is intended to be worn externally to the patient's body. The EPG connects to one end of one or more percutaneous, or skin-penetrating, leads. The other end of the percutaneous lead is implanted within the body and incorporates multiple electrode surfaces analogous in function and use to those of an implanted lead.

The external charger 40 of the medical device system 20 provides electrical power to the IPG 70. The electrical power may be delivered through a charging coil 90. The IPG 70 may also incorporate power-storage components such as a battery or capacitor so that it may be powered independently of the external charger 40 for a period of time, for example from a day to a month, depending on the power requirements of the therapeutic electrical stimulation delivered by the IPG.

The patient programmer 50 and the clinician programmer 60 may be portable handheld devices that can be used to configure the IPG 70 so that the IPG 70 can operate in a certain way. The patient programmer 50 is used by the patient in whom the IPG 70 is implanted. The patient may adjust the parameters of the stimulation, such as by selecting a program, changing its amplitude, frequency, and other parameters, and by turning stimulation on and off. The clinician programmer 60 is used by a medical personnel to configure the other system components and to adjust stimulation parameters that the patient is not permitted to control, such as by setting up stimulation programs among which the patient may choose, selecting the active set of electrode surfaces in a given program, and by setting upper and lower limits for the patient's adjustments of amplitude, frequency, and other parameters.

In the embodiments discussed below, the clinician programmer 60 is used as an example of the electronic programmer on which the advanced virtual reality representation of medical devices can be displayed. However, it is understood that the advanced virtual reality representation of medical devices according to the present disclosure may also be displayed on the patient programmer 50 or other touch screen programming devices (such as smart-phones or tablet computers) in other embodiments. Regardless of the programming device used, the advanced virtual reality representation of medical devices of the present disclosure is implemented through a touch screen or touch-sensitive user interface installed on the programming device.

FIGS. 2-13 are various screenshots of an example user interface 100 that illustrates various aspects of the advanced virtual reality representation of medical devices according to the present disclosure. In more detail, referring to FIG. 2, the user interface 100A displays a virtual reality representation of an anatomical environment 110 (also referred to as anatomical surroundings) of a patient. The virtual reality representation of the anatomical environment 110 may involve 3-D or 2-D models. In the embodiment shown in FIG. 2, the anatomical environment 110 includes a portion of a spine. In other embodiments, the anatomical environment 110 may include other parts of the human body, for example the brain, the heart, or the abdomen, etc.

In some embodiments, the patient's physiological data (for example the patient's height or weight) is obtained by detecting user input through the user interface 100. In other embodiments, the patient's physiological data may be obtained or through another suitable mechanism such as from an electronic database, which can be remote or local to the programmer. According to the various aspects of the present disclosure, the virtual reality representation of the anatomical environment 110 may be customized in response to the patient's physiological data. For example, the spine (or another implementation of the anatomical environment) may be scaled based on the height of the patient.

The user interface 100A also includes a graphical display 120 that shows an entire human body (simulating the patient's body). A portion of the human body corresponding to the anatomical environment 110 is highlighted by a box superimposed on the human body. The user can quickly access a particular location of the human body by moving the box to that location. As the box is being moved, the anatomical environment 110 is updated to reflect the change. The user interface 110A also offers a zoom feature 125 that can be used to show a closer view (by zooming in) or a farther view (by zooming out) of the human body in the graphical display 120. In other words, when the zoom feature 125 is activated to zoom in the human body, a more detailed view (e.g., showing fewer vertebrae) of the anatomical environment 110 is shown. Conversely, when the zoom feature 125 is activated to zoom out of the human body, a less detailed view (e.g., showing more vertebrae) of the anatomical environment 110 is shown.

The user interface 100A further includes a digital carousel 130 that shows the virtual reality representations of a plurality of medical devices. The virtual reality representation of each medical device may include an accurate movable and rotatable 3-D model of the medical device. The medical devices may be of different types, for example different types of leads, paddles, and pulse generators (including both implantable pulse generators (IPG) and external pulse generators (EPG).) These different types of medical devices are arranged in the carousel 130, which is spinnable. As the user spins the carousel 130, for example by moving his finger to the left or right on the touch screen, the models of different medical devices may be brought to the front of the carousel 130. The medical device at the front of the carousel 130 may be considered an active selection of the user (i.e., the device is activated).

Figure 2:
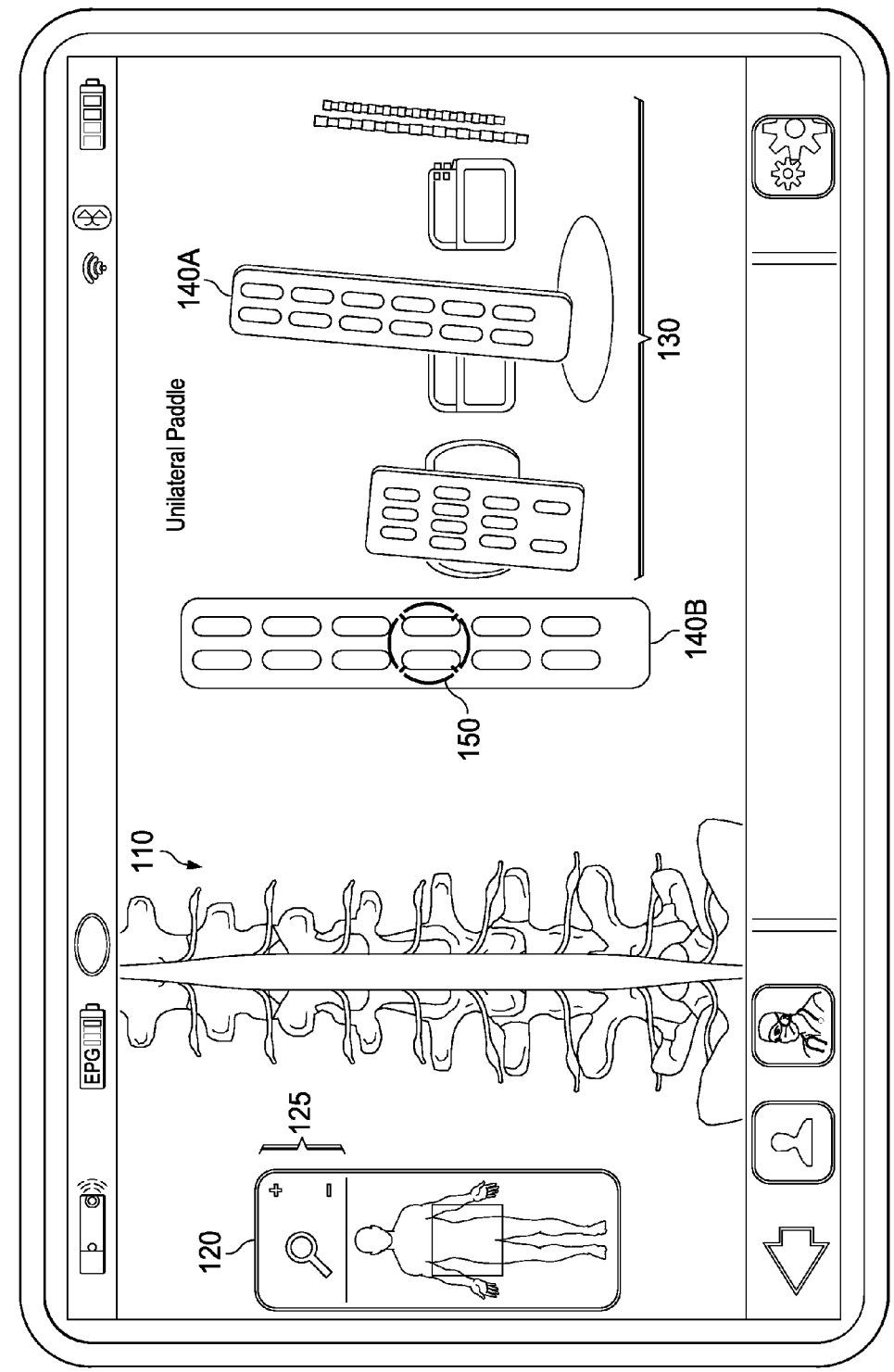
FIGS. 2-13 are various example user interfaces for visualizing medical devices according to various aspects of the present disclosure.

Once a medical device is selected/activated through the carousel 130, it can be dragged outside of the carousel 130 (for example to the left of the carousel 130 in FIG. 2) for further customization and manipulation. For example, the medical device shown to be at the front of the carousel 130 in FIG. 2 is a "Unilateral Paddle" 140A in FIG. 2. A larger copy of the activated medical device Unilateral Paddle 140B can be displayed in another part of the screen. In some embodiments, a cursor 150 on the Unilateral Paddle 140B indicates the present location of the user's finger.

Figure 3:
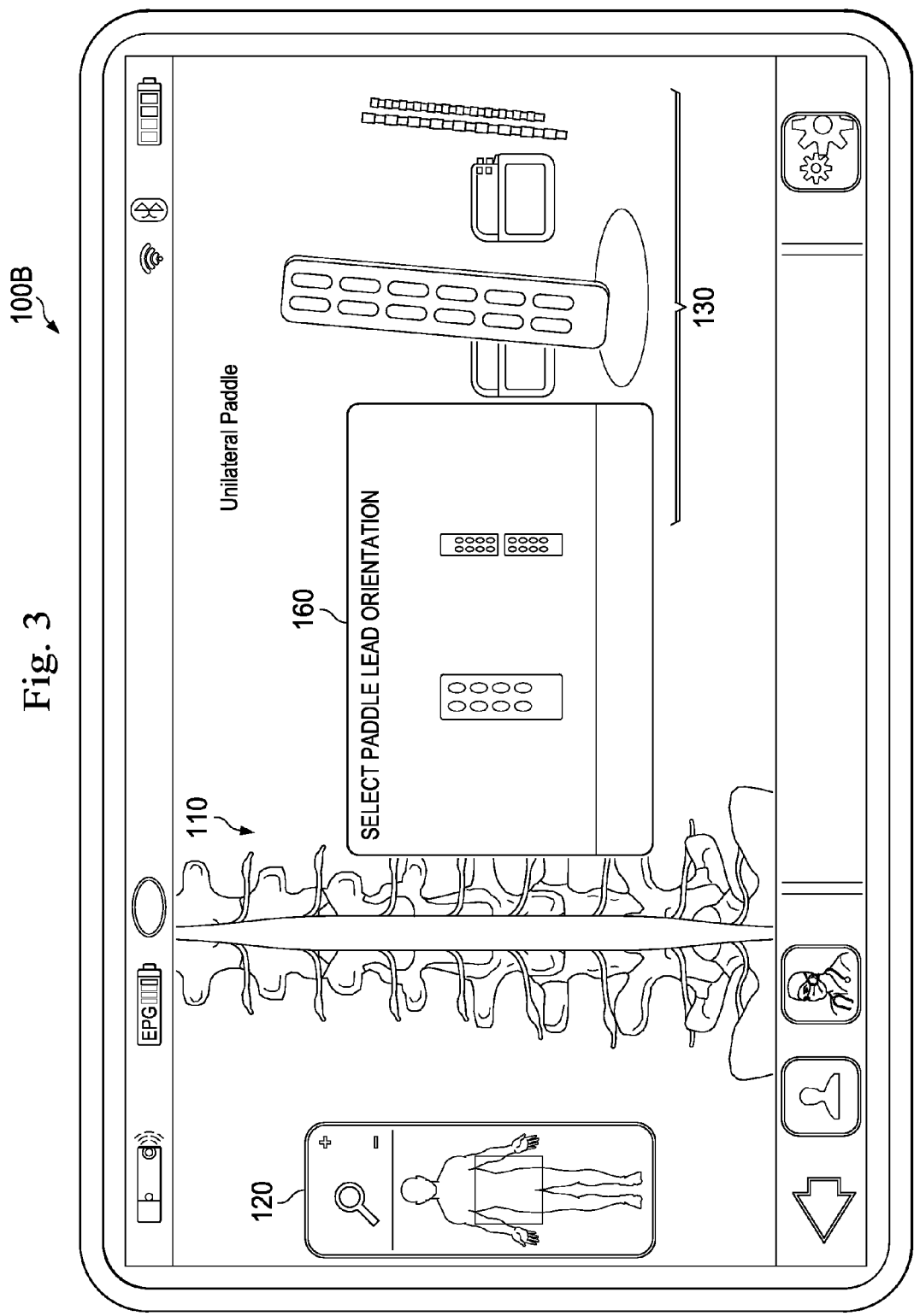
Figure 4:
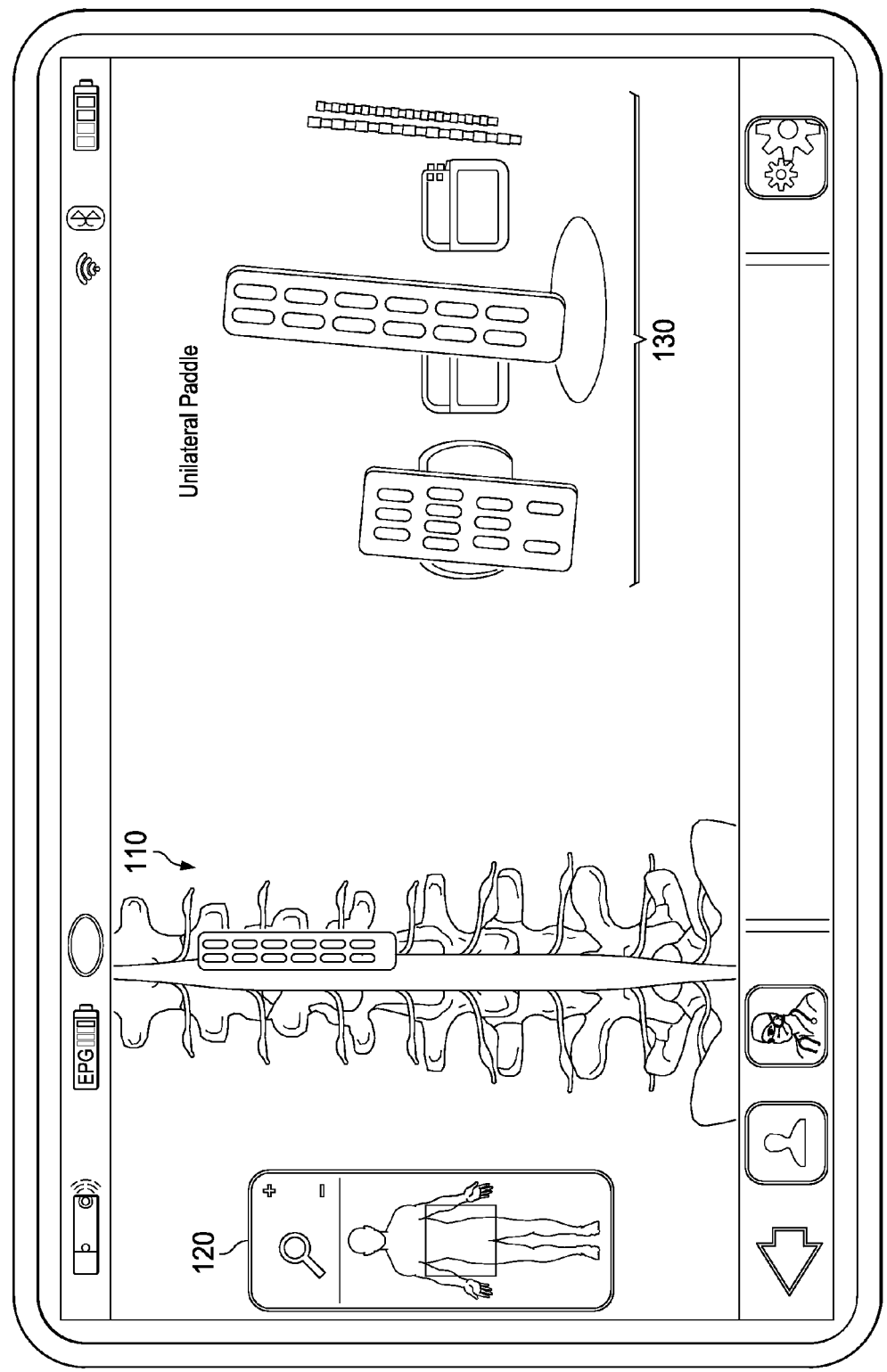
Figure 5:
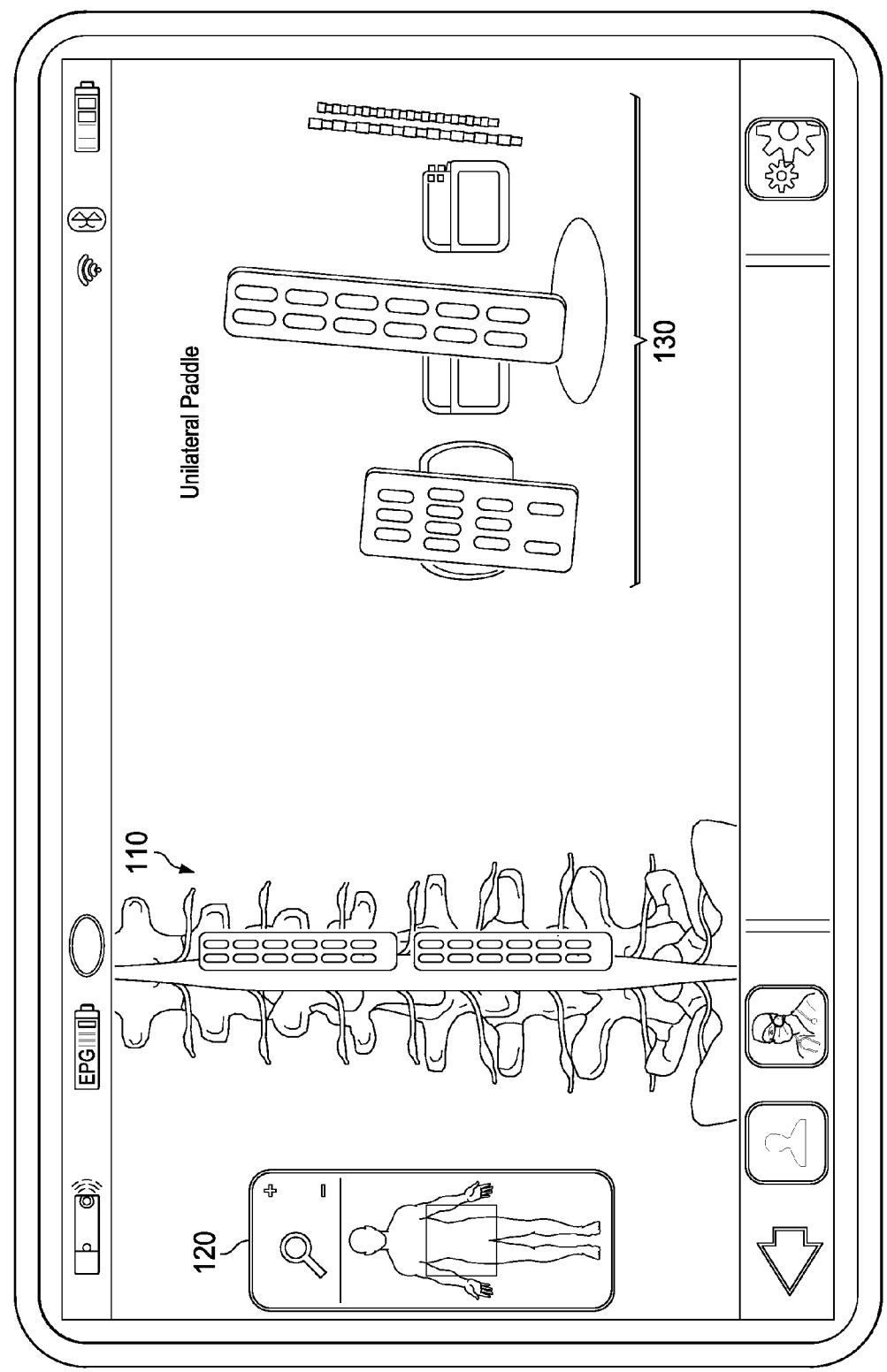
Figure 5A:
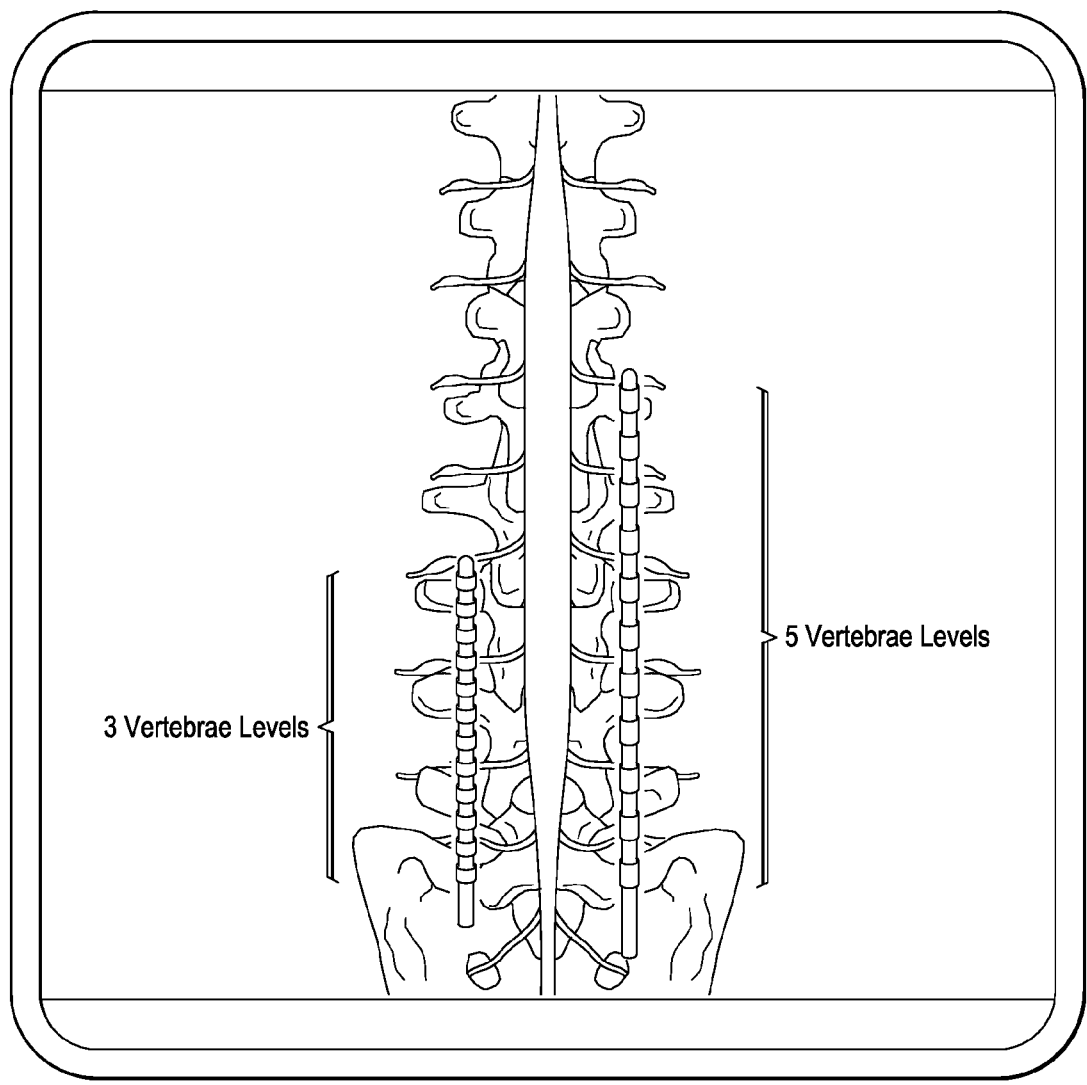

Referring now to FIG. 3, once the user has selected the applicable medical device, the user interface 100B may prompt the user to further customize the selected medical device. In some embodiments, the customization of the selected medical device may include setting a relational pattern of the selected medical device. This may be done via a pop-up window 160. For example, the pop-up window 160 may display two types of lead patterns: a single lead pattern and a double lead pattern. The user may select the desired lead pattern through a gesture-based input via the touch screen. FIG. 4 illustrates the result if a single lead pattern is selected, and FIG. 5 illustrates the result if a double lead pattern is selected. The virtual reality representation for either the single lead or the double lead may be placed on the virtual reality representation of the spine. It is understood that the relational patterns are not restricted to the two types of lead patterns discussed above, nor are they specific to any medical device. Furthermore, the user interface may allow for additional customization of the selected medical device. For example, contact spacing may be customized, which can vary from lead to lead, especially in percutaneous leads. This affects the number of vertebrae a single lead may cover because of the spacing between contacts. A visual example illustrating the customization of contact spacing or lead spacing is shown in FIG. 5A.

Figure 6:
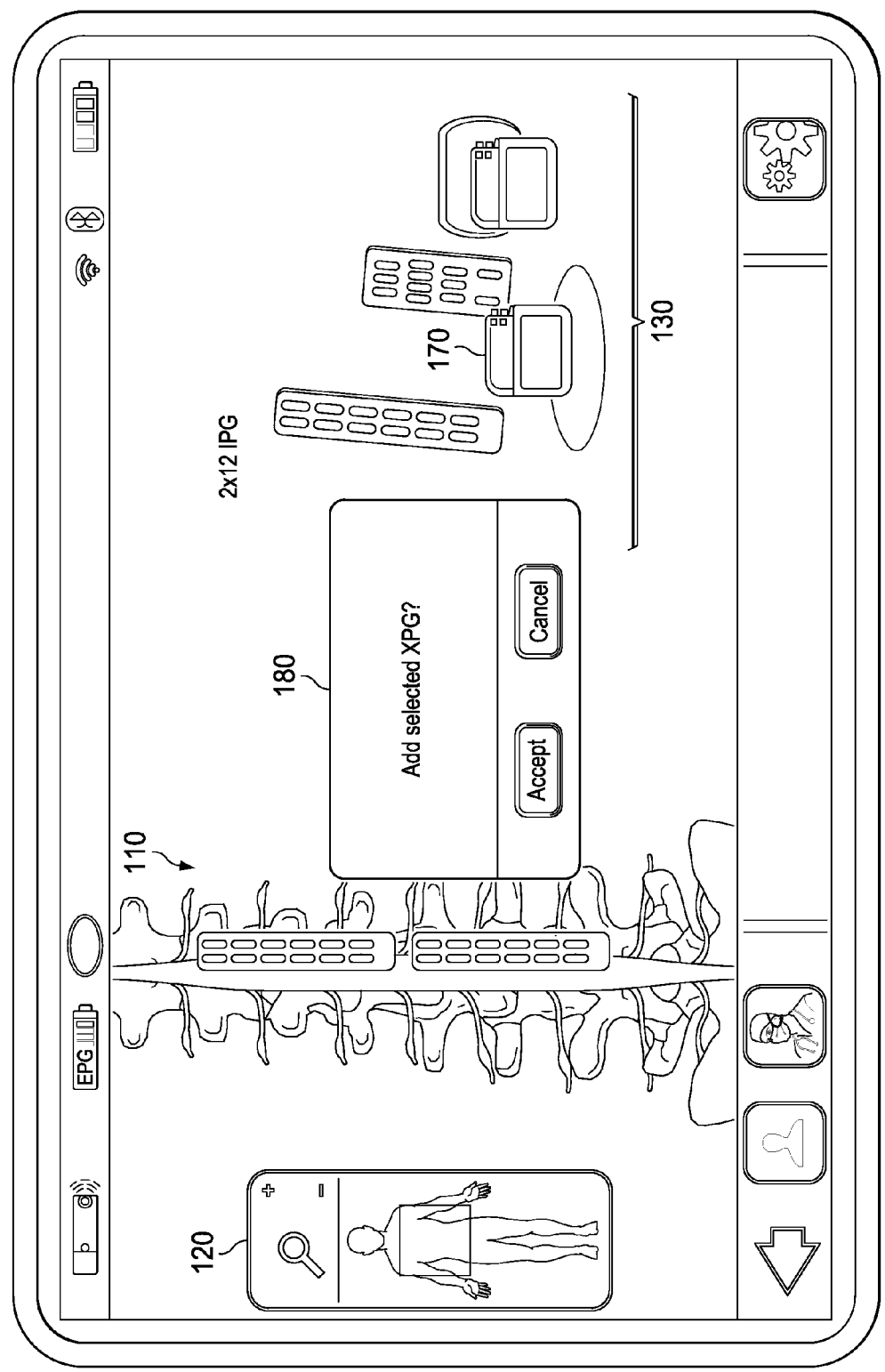

Referring now to FIG. 6, after the selected medical device has been customized, the user interface 100E allows another medical device to be selected through the digital carousel 130, for example a pulse generator 170. Simulated connections may reduce potential errors by checking to see if the lead is compatible with the connector is it being plugged into. In the embodiment shown in FIG. 6, the selected pulse generator is a 2×12 IPG, meaning that the pulse generator 170 has two bores and twelve electrodes. A dialog window 180 may be displayed to ask the user to verify the selection.

Figure 7:
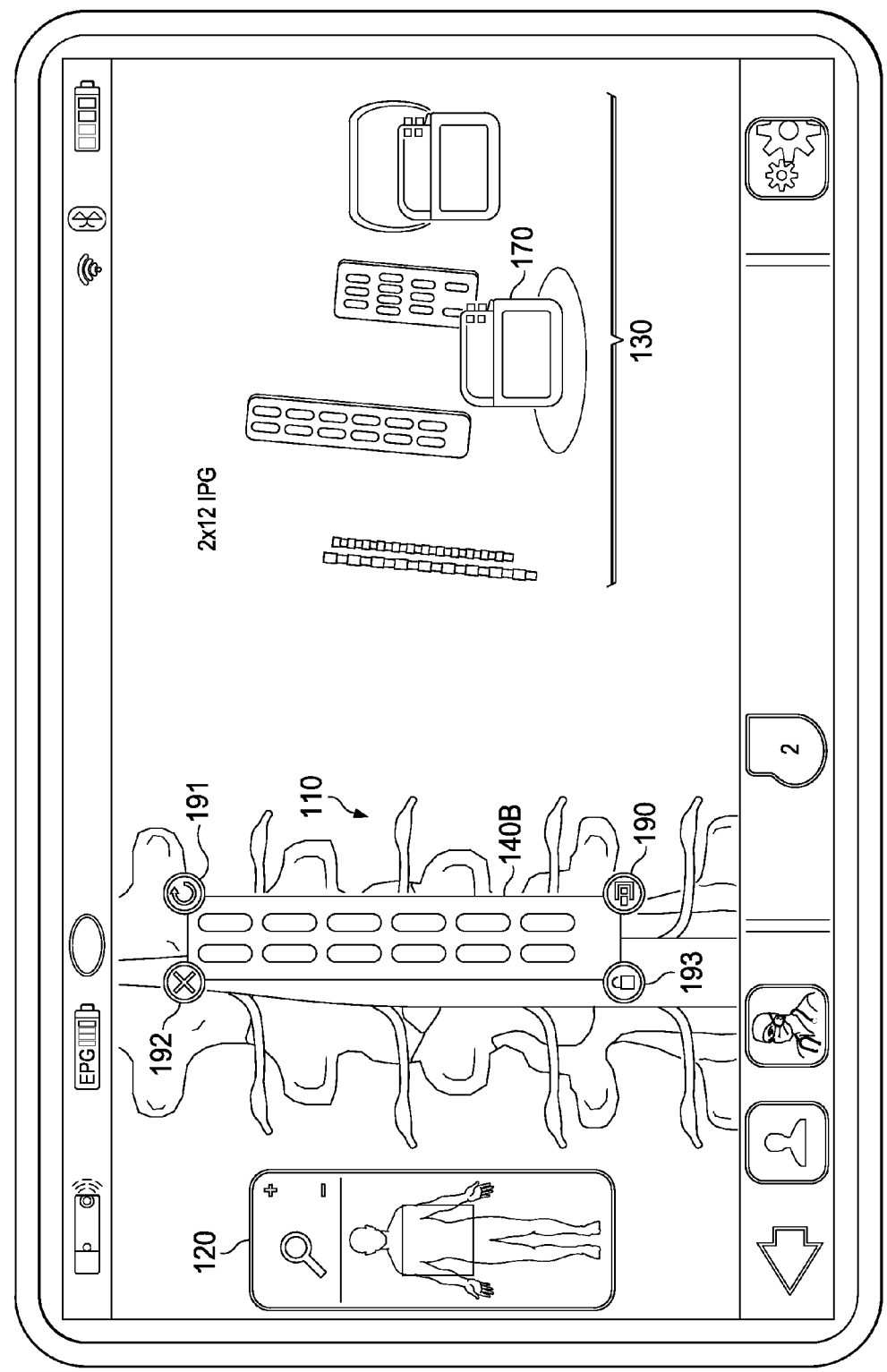

Referring now to FIG. 7, after the pulse generator 170 has been added, the user interface 100F may allow the user to make simulated connections (or coupling) between the Unilateral Paddle 140B and the pulse generator 170. In certain embodiments, the user interface 100F employs an edit menu to carry out the simulated connections. The edit menu contains a plurality of icons that can each be used to perform a certain task. In the illustrated embodiment, the icons include a "connect to pulse generator" icon 190, a "rotate" icon 191, a "delete" icon 192, and a "lock" icon 193. As the names of these icons indicate, the "connect to pulse generator" icon 190 allows a simulated connection to be made between the Unilateral Paddle 140B and the pulse generator 170; the "rotate" icon 191 allows the Unilateral Paddle 140B to be rotated; the "delete" icon 192 allows the Unilateral Paddle 140B to be removed from the touch screen display; and the "lock" icon 193 allows the Unilateral Paddle 140B to be locked (i.e., to prevent further movement or modification of the Unilateral Paddle 140B).

Figure 8:
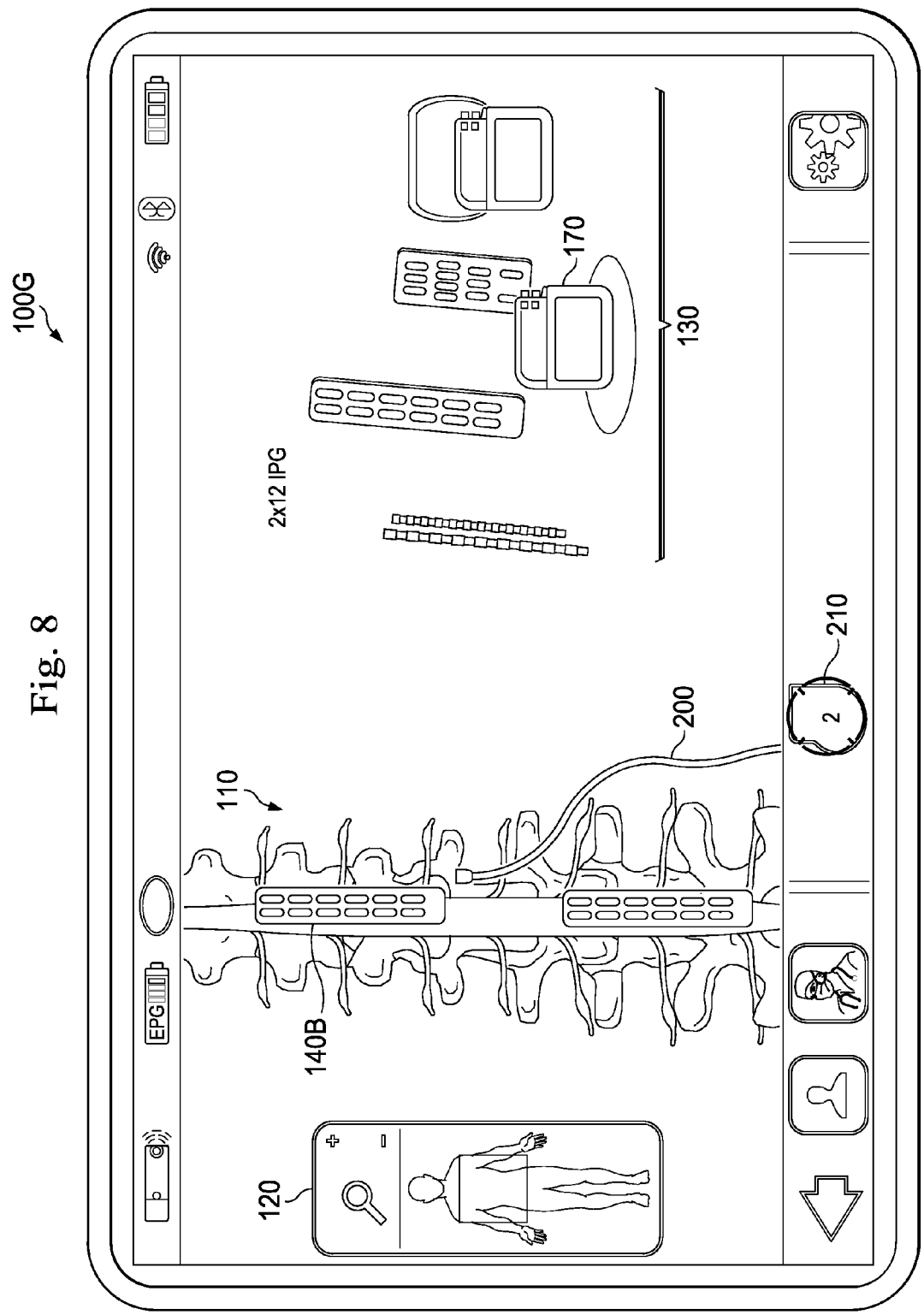

Referring now to FIG. 8, using the edit menu discussed above (specifically, the "connect to pulse generator" icon 190), the user may draw a simulated connection 200 between the Unilateral Paddle 140B and the pulse generator 170. For example, after the "connect to pulse generator" icon 190 is pressed, the user may hold and drag a line between the Unilateral Paddle 140B and the pulse generator 170 to establish the simulated connection 200. In some embodiments, the pulse generator 170 may be represented by an icon 210. In FIG. 8, the icon displays the number "2", which indicates the number of bores the pulse generator 170 contains. In this case, the simulated connection 200 is drawn between the Unilateral Paddle 140B and the icon 210.

Figure 9:
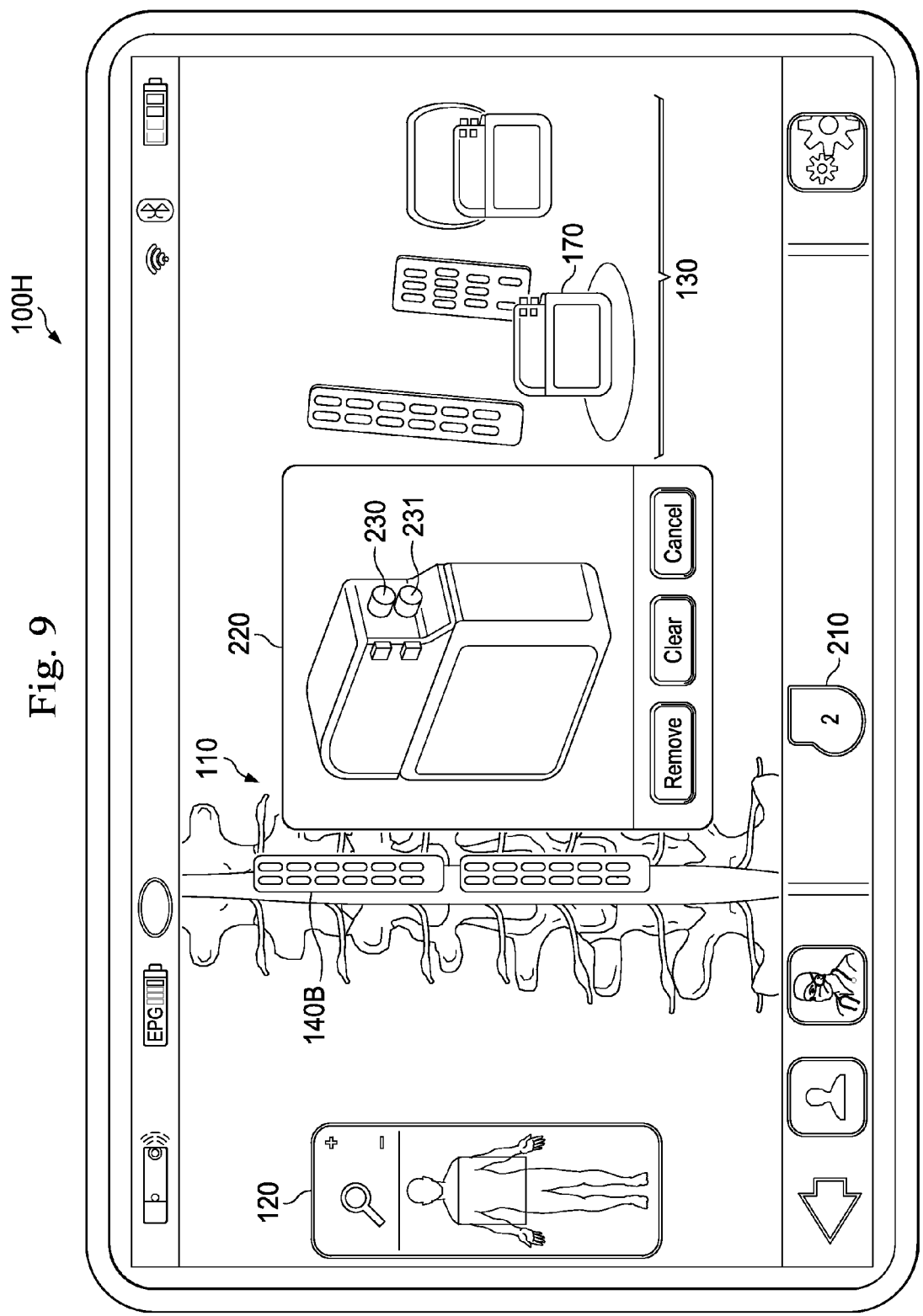
Figure 10:
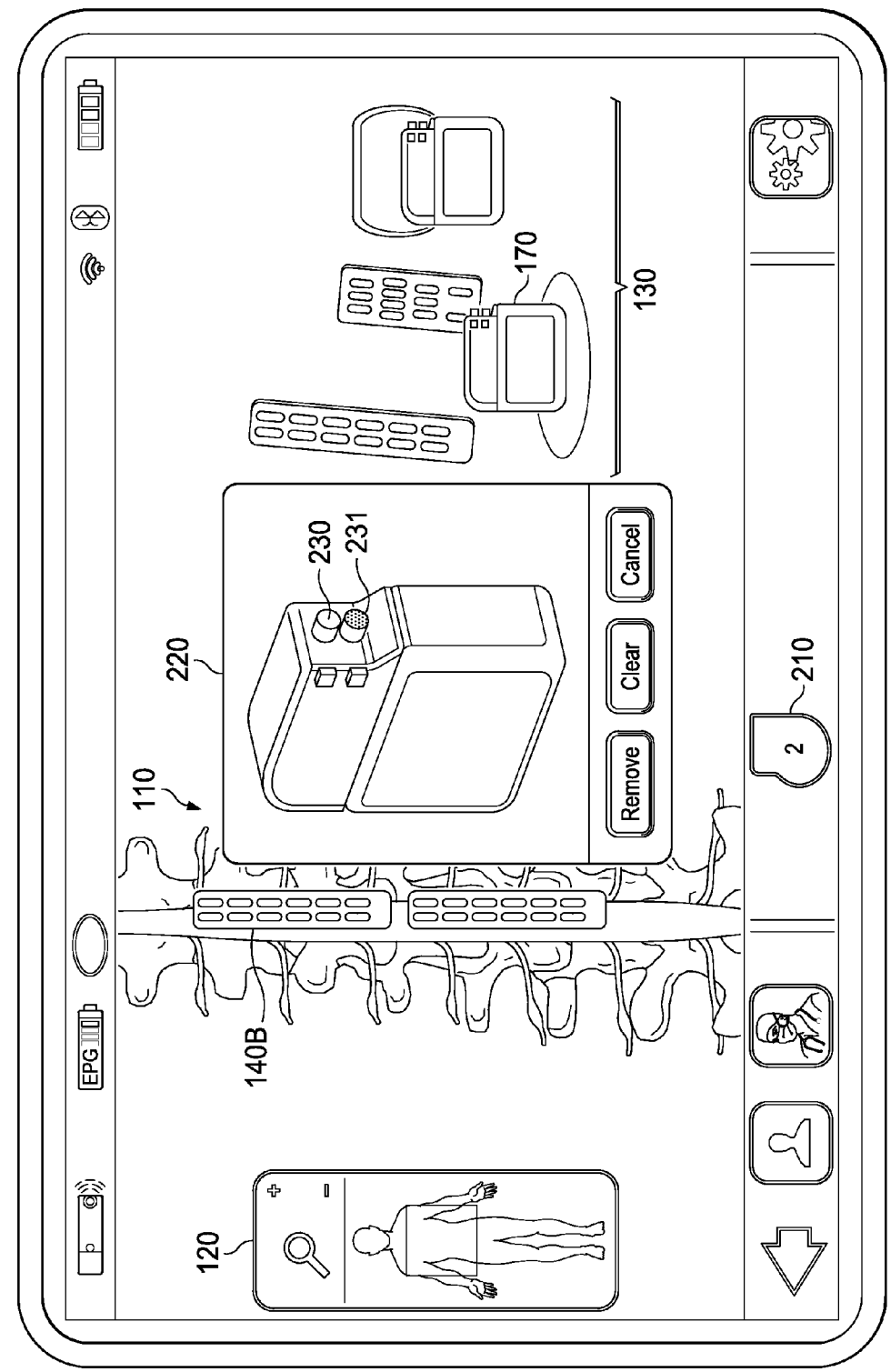

Referring now to FIG. 9, after the simulated connection 200 is drawn, the user interface 100H may display another pop-up window 220 that shows a detailed virtual reality representation of the pulse generator 170. The pulse generator 170 shown in the pop-up window 220 may clearly illustrate the two bores 230 and 231. The user may select the desired bore 230/231 to be connected to the Unilateral Paddle 140B by touching the bore 230/231 on the pop-up window 220. As an example, the user selects the bore 231, which then becomes highlighted to indicate its selection, as shown in FIG. 10.

Figure 11:
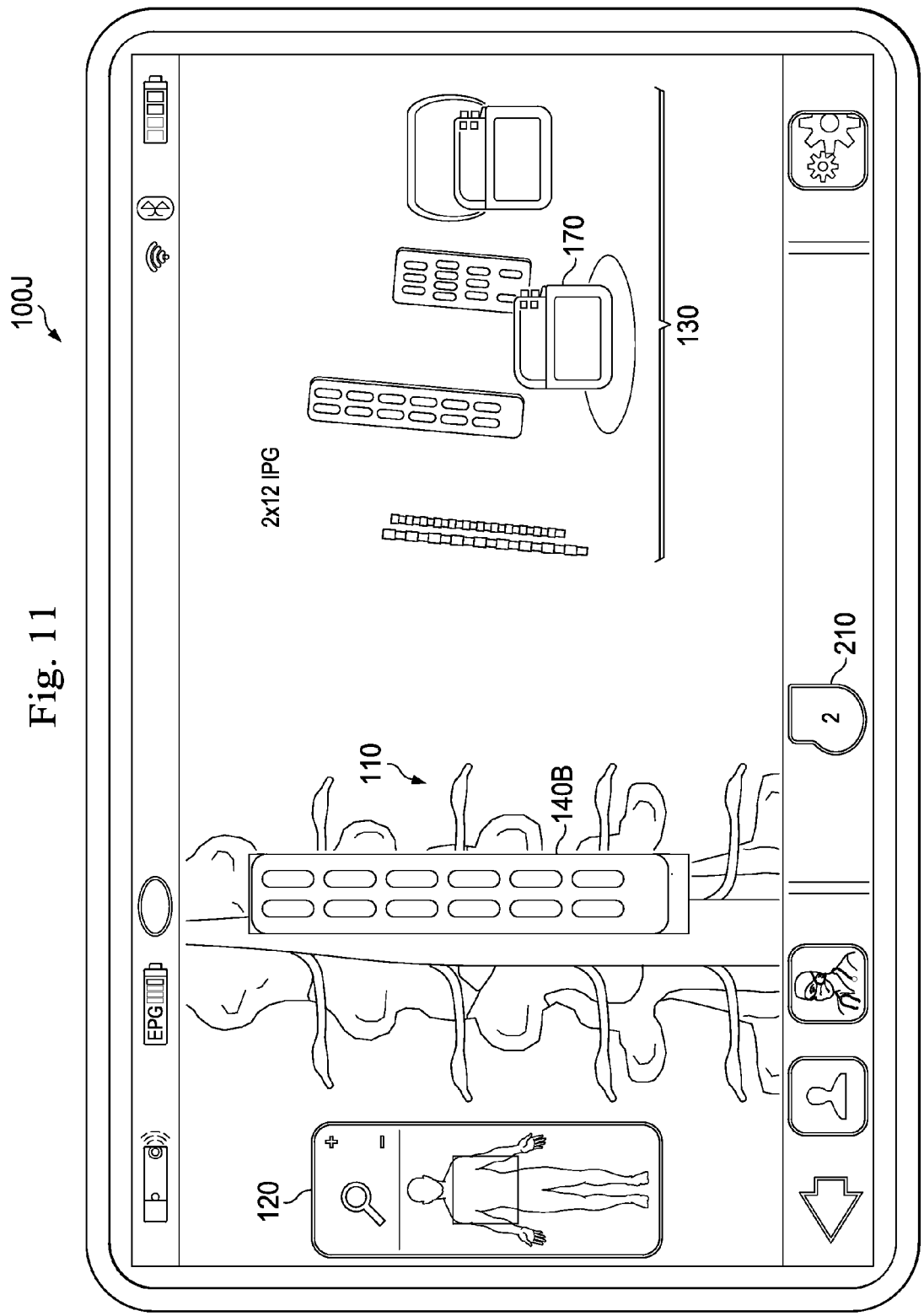

Referring now to FIG. 11, after the desired bore has been selected, the simulated connection between the Unilateral Paddle 140B and the pulse generator is complete. The Unilateral Paddle 140B may be highlighted (or emphasized through another suitable visual means) to signify that a simulated connection has been established thereto.

Figure 12:
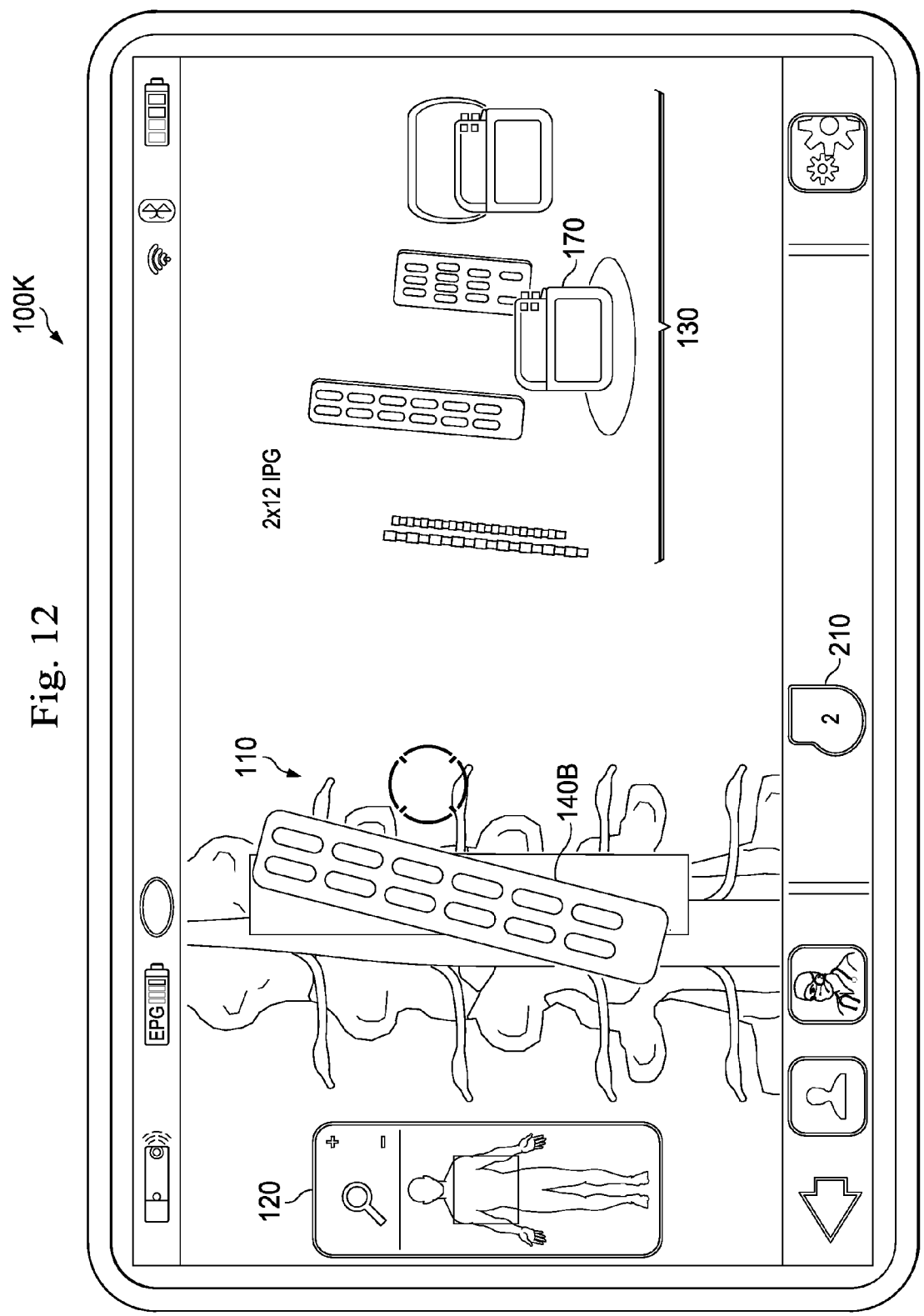

Referring now to FIG. 12, the orientation of the Unilateral Paddle 140B (or any other selected medical device) may be adjusted via the "rotate" icon 191 (shown in FIG. 7). In the illustrated embodiment, the Unilateral Paddle 140B is rotated clockwise. It is understood that the rotation may occur in multiple planes, such as in the coronal plane, or towards the user, etc.

Although not specifically shown for reasons of simplicity, it is understood that additional manipulations may be done to a selected medical device (e.g., the Unilateral Paddle 140B). For example, the selected medical device may be scaled in size or moved to a different position with respect to the anatomical environment 110 (e.g., up or down the spine). In addition to showing simulated connections, it is also understood that these virtual reality representations discussed above, upon being touched, may offer ample information about the object being touched. For example, if a virtual reality representation of an xPG is touched, the serial number and other details regarding the xPG may be displayed. This is true with leads and/or implants as well.

Figure 13:
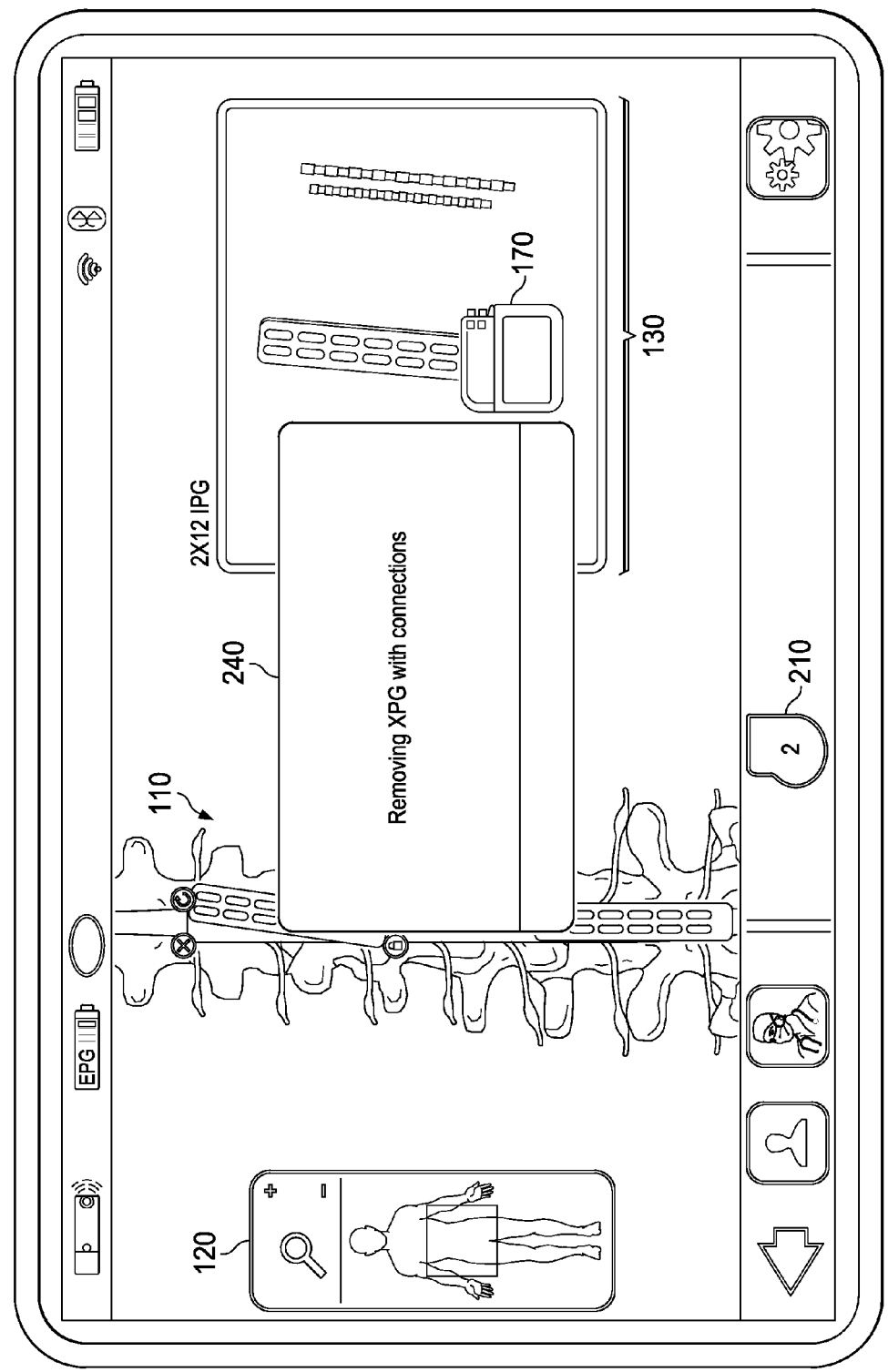

Referring to FIG. 13, the user interface 100L may also display one or more "failsafe" messages to the user, so as to alert the user of a situation that warrants attention. For example, the user interface 100L may display a dialog window 240 to let the user know when a pulse generator is deleted. Other situations may include when multiple connections are made or wrong/impermissible connections are made. This includes mismatch between stimulation lead and IPG bore or the trial connector block. Another instance is switching off stimulation when moving from a stimulation program 1 to a program 2 to avoid potential electric shock to the patient. Yet another one is stopping stimulation when selecting the patient pain mapping screen to avoid a false drawn pain area. Another instance prevents removing xPGs that are connected to stimulation leads, unless the lead connections are removed first. However, these failsafe messages are not necessarily an indication that something is wrong. Rather, in some cases they are provided to give a "heads up" to the user when one or more predefined events are detected, wherein these predefined events may indicate a potential problem. In this manner, the user may be less likely to make an inadvertent mistake. In some embodiments, the failsafe message may also be communicated to the user not necessarily by visual display but by other mechanisms, for example through audio communication.

It is understood that the virtual reality representations of the various medical devices are not restricted to the ones shown on the screen. As technology continues to advance, updated representations of existing or new medical devices may be imported into the user interface 100 or example through the use of a memory card or a wireless download.

Figure 14:
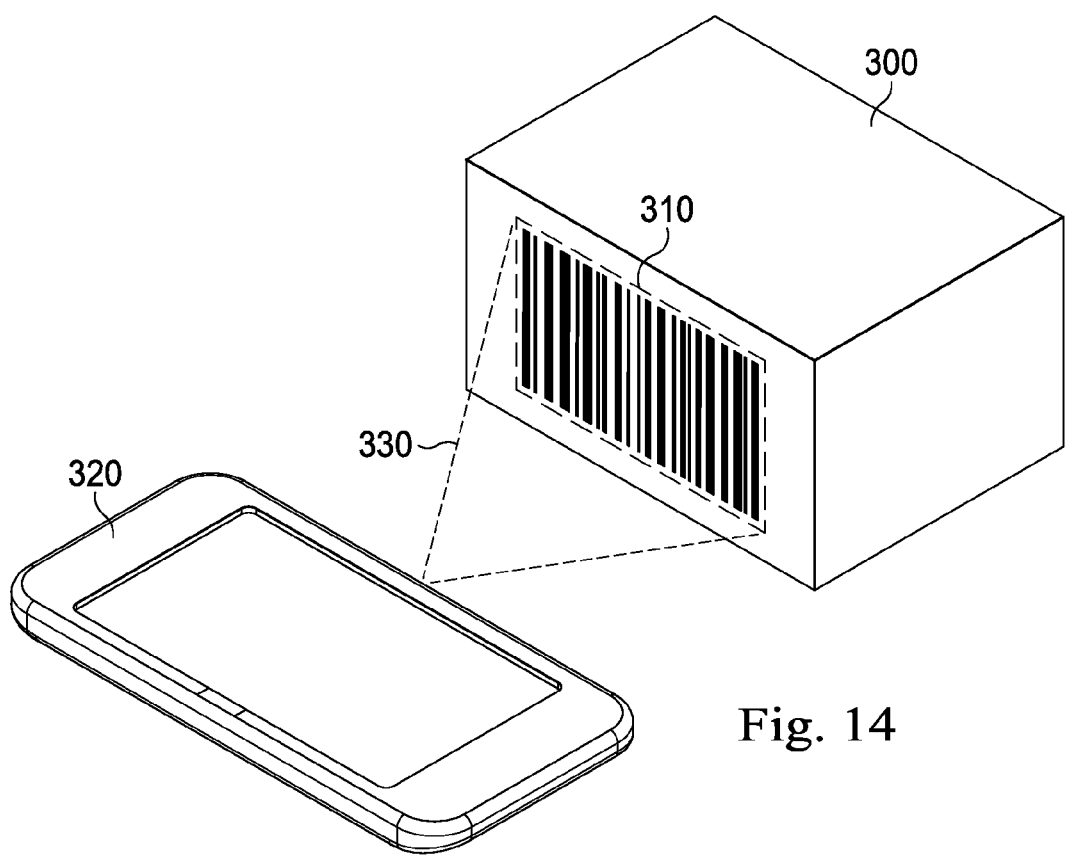
FIG. 14 is a block diagram illustrating how a virtual representation of a medical device can be obtained according to various aspects of the present disclosure.

In the discussions above, the virtual reality representation of a desired medical device may be selected from a spinnable digital carousel containing the models for a plurality of medical devices. However, this is not the only method of selecting the virtual reality representation of the desired medical device. Referring to FIG. 14, the virtual reality representation of the desired medical device may also be achieved by scanning the desired medical device. For example, a desired medical device such as an IPG may be located inside a box 300. A digital identifier 310 of the medical device may be displayed on the box 300. The digital identifier 310 may be a barcode or a Quick Response (QR) code, for example.

An electronic device 320 with imaging capabilities may be used to scan the digital identifier 310 by way of a radiation beam 330. In some embodiments, the electronic device 320 may be a clinician programmer, which includes a camera that can be used to perform the scanning. A more detailed discussion of selecting the virtual reality representation of the desired medical device via scanning is found in U.S. patent application Ser. No. 13/600,684, filed on Aug. 31, 2012, titled "Systems and Methods for the Identification and Association of Medical Devices", the contents of which are incorporated herein by reference in its entirety.

As the digital identifier 310 is scanned into the electronic device 320, the electronic device 320 may search an electronic database (which may be internal to the electronic device 320 or may be cloud-based) and match the digital identifier 310 with a corresponding medical device. Thereafter, the virtual reality representation of that corresponding medical device is automatically chosen and displayed through the user interface discussed above. In other words, the medical device selection process through the carousel is bypassed. The digital identifier 310 (e.g., barcode) can also contain digital 3-D information of the item needed to render the item in the clinician programmer. For example, suppose a scan of a barcode generates an implantable medical device that is not in the catalog of the clinician programmer. Therefore, the clinician programmer can extract the information from the barcode content and add it to the catalog including its 3-D representation among other information.

Figure 15:
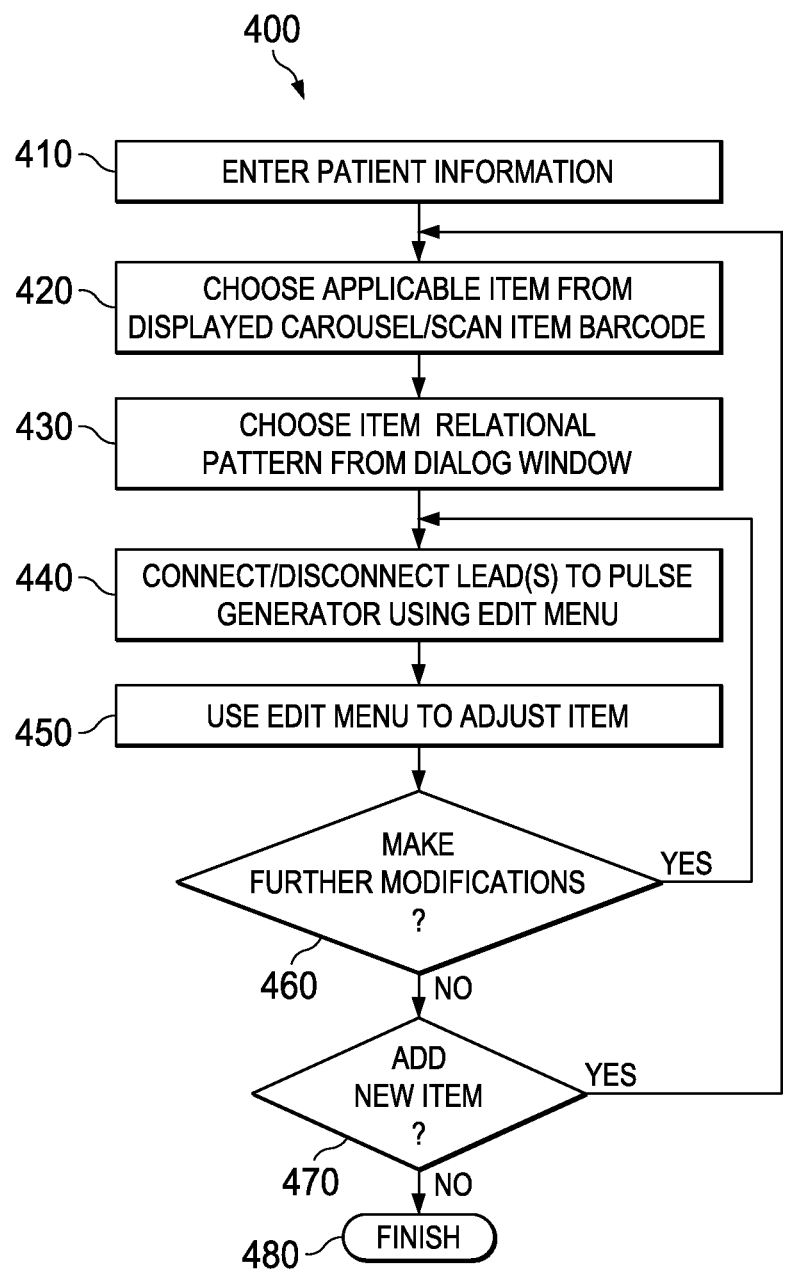
FIGS. 15-16 are flowcharts of methods for visualizing one or more medical devices according to various aspects of the present disclosure.

According to various aspects of the present disclosure, FIG. 15 illustrates a method 400 of interacting with the user interface having the virtual reality representation of medical devices. The method 400 includes a step 410, in which patient information is entered. The patient information may include data such as the patient's height, weight, age, gender, medical history, and other relevant information. The patient information may be pulled from an electronic database (either local or in an electronic "cloud") or may be gathered from the patient directly. The patient information is entered into an electronic programmer such as a clinician programmer.

The method 400 proceeds to a step 420, in which an applicable item is chosen. The applicable item is a desired medical device for example. In some embodiments, the medical device may be selected from a digital carousel that virtually represents a plurality of different types of medical devices. In other embodiments, the medical device may be selected by scanning a digital identifier (such as a barcode or a QR code) associated with the medical device.

The method 400 proceeds to a step 430, in which a relational pattern is chosen for the selected medical device. As an example, the relational pattern may involve, but is not limited to, the selection between a single or double lead pattern for a paddle lead. In other embodiments, the medical device may be customized in other ways besides choosing a relational pattern.

The method 400 proceeds to a step 440, in which an additional medical device is selected, and an interaction between these medical devices is established. For example, the first medical device (selected in step 420) is a lead, and the second medical device selected in step 440 is a pulse generator. Therefore, a simulated connection may be established between the lead and the pulse generator in step 440.

The method 400 proceeds to a step 450, in which an edit menu is used to adjust the medical device. The edit menu may include a plurality of icons that each correspond to a particular manipulation of the medical device. For example, these icons may include connect, rotate, delete, or lock icons, which can be used respectively to: make simulated connections, perform rotations, remove the representation of, and prevent modification of, the virtual reality representation of the medical device.

The method 400 proceeds to a step 460, which is a decision step to determine whether further modifications are needed. If the answer is yes, then the method 400 loops back to the step 440. If the answer is no, then the method 400 proceeds to another decision step 470 to determine whether new item(s) (i.e., new medical devices) need to be added. If the answer is yes, then the method 400 loops back to the step 420. If the answer is no, then the method 400 proceeds to step 480 to finish the method 400. It is understood that the steps 410-480 described herein are merely example steps according to an embodiment. These steps may be omitted or modified in certain embodiments. In certain other embodiments, the method 400 may also include additional steps performed before, during, or after the steps 410-470.

Figure 16:
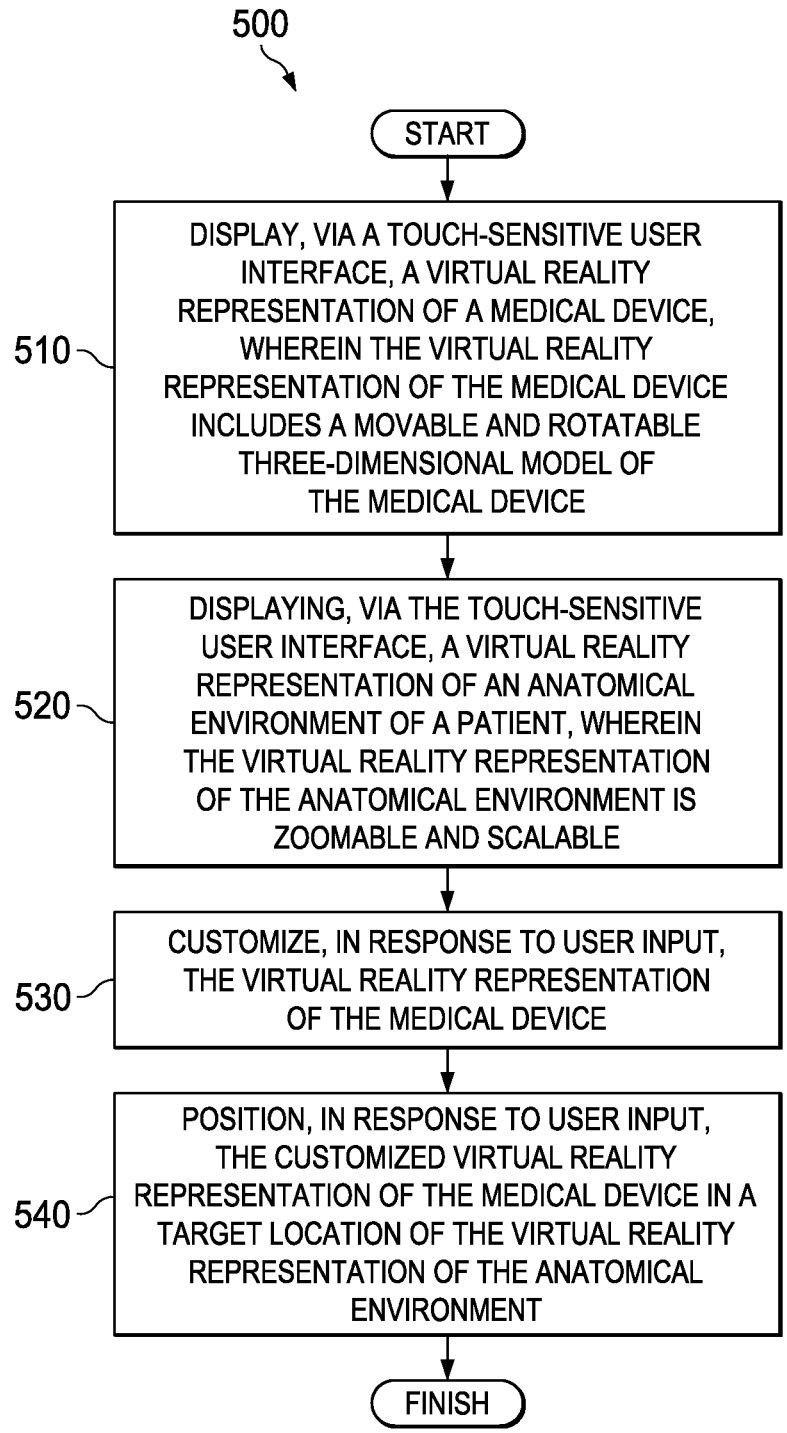

FIG. 16 is a flowchart of a method 500 for facilitating visualization in a medical context according to various aspects of the present disclosure. The method 500 includes a step 510, in which a virtual reality representation of a medical device is displayed via a touch-sensitive user interface. In some embodiments, the touch-sensitive user interface is displayed on a touch-sensitive screen of a portable electronic device with wireless communication capabilities. As examples, the portable electronic device may include one of: a clinician programmer, a patient programmer, and a computer tablet.

In some embodiments, the virtual reality representation of the medical device includes a movable and rotatable 3-D model of the medical device. The 3-D model of the medical device may also be lockable and removable. In some embodiments, the step 510 includes offering virtual reality representations of a plurality of different types of medical devices on a spinnable digital carousel, and then selecting, in response to user input, a first medical device from the digital carousel to be customized. The different types of medical devices may include, as examples, implantable pulse generators, external pulse generators, and different types of leads. In some embodiments, the step 510 further includes selecting a second medical device different from the first medical device, and establishing a simulated coupling between the first and second medical devices.

The method 500 includes a step 520, in which a virtual reality representation of an anatomical environment of a patient is displayed via the touch-sensitive user interface. In some embodiments, the virtual reality representation of the anatomical environment is zoomable and scalable.

The method 500 includes a step 530, in which the virtual reality representation of the medical device is customized in response to user input. In some embodiments, the step 530 includes setting a relational pattern of the virtual reality representation of the medical device.

The method 500 includes a step 540, in which the customized virtual reality representation of the medical device is positioned in a target location of the virtual reality representation of the anatomical environment in response to user input.

It is understood that the method 500 may include additional steps that are performed before, during, or after the steps 510-540 discussed above. For example, in some embodiments, the method 500 may include an additional step before the step 510, in which a digital identifier is detected in response to an image scan. The digital identifier may include a barcode or a Quick Response (QR) code associated with the medical device. Thereafter, the digital identifier is matched to a corresponding medical device. The corresponding medical device is the medical device whose virtual reality representation is to be displayed. As another example, the method 500 may include an additional method step that communicates a failsafe message in response to a detection of one or more predefined events.

The virtual reality representation of medical devices according to the various aspects of the present disclosure offers advantages over existing methods of representing medical devices. It is understood, however, that not all advantages are discussed herein, different embodiments may offer different advantages, and no embodiment is limited to particular advantages.

One advantage of the present disclosure is that the virtual reality representation of medical devices is done using flexible and accurate 3-D models. The 3-D models can be rotated, moved, scaled, or otherwise manipulated, so as to give the user an accurate view of a selected medical device. Thus, the user (for example a surgeon) no longer needs to picture the medical device in his head. Instead, the user can examine the medical device in detail through the virtual reality representation and understand exactly how the medical device can be deployed.

Similarly, another advantage of the present disclosure is that it illustrates an interaction between the medical devices with respect to their intended anatomical surroundings via their virtual reality representations. The anatomical surroundings may be scaled up or down or zoomed in or out. The virtual reality representation of the medical devices can also be positioned anywhere within the anatomical surroundings. In this manner, a user can achieve a desired view of the medical device in the target anatomical surroundings. For example, a surgeon may get a preview of what it would "look like" if he placed a certain configuration of a paddle lead in a specific location of a spine. If the surgeon is not satisfied with such preview, he can easily tweak the orientation or the position of the lead with respect to the spine, until he is satisfied by the result. The surgeon no longer needs to attempt to visualize the interaction between these devices and the anatomical surroundings in his mind.

Other advantages of the present disclosure involve the capability to customize and manipulate the virtual reality representation of the medical devices. For example, a relational pattern may be set for the medical device, and the medical device can be rotated, locked, or deleted. Furthermore, the present disclosure offers the capability to communicate "failsafe" messages to the user in order to prevent inadvertent mistakes. These features make the virtual reality user interface of the present disclosure more flexible and more powerful, and thus more practical for the user.

Figure 17:
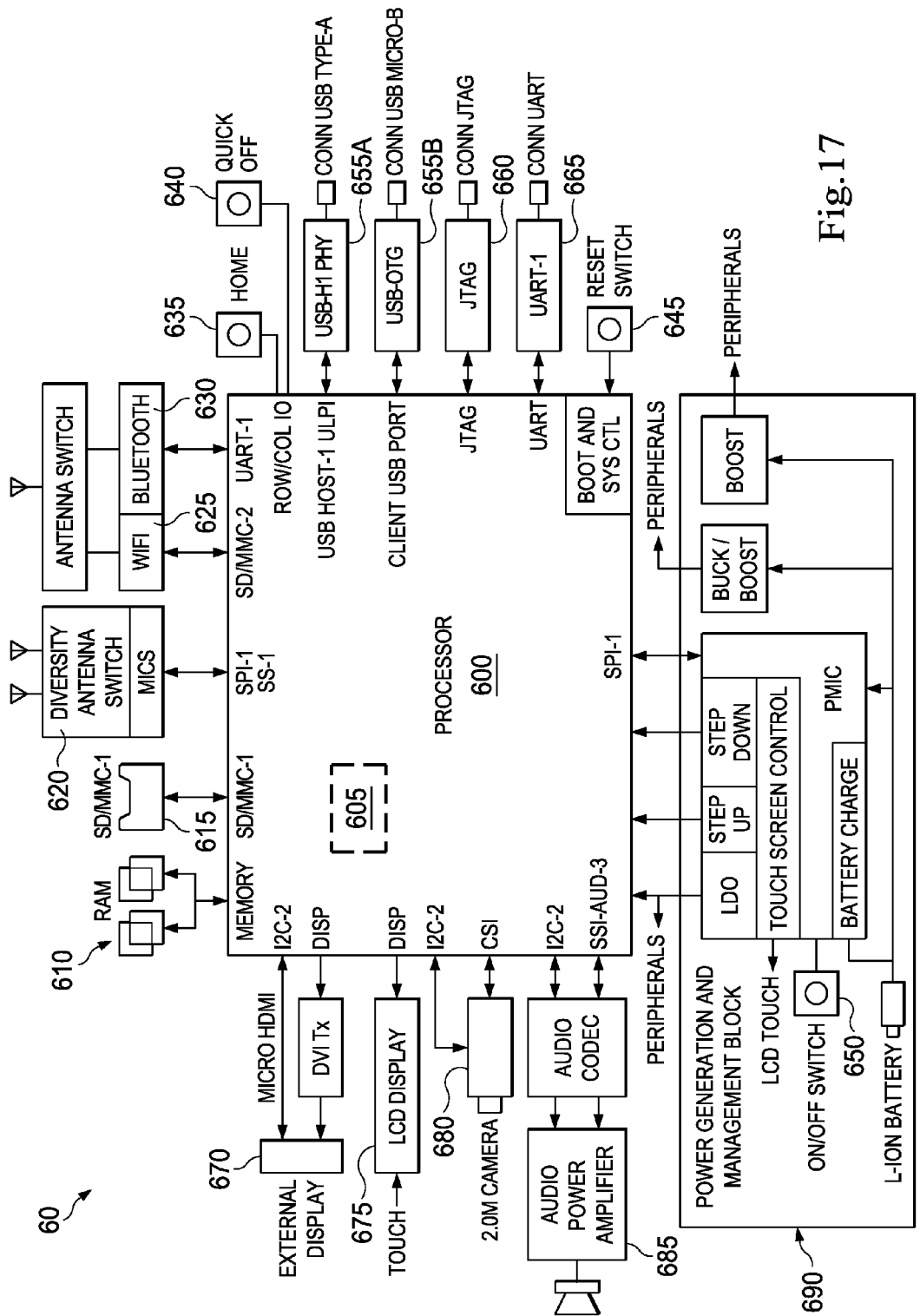
FIG. 17 is a simplified block diagram of an electronic programmer according to various aspects of the present disclosure.

FIG. 17 shows a block diagram of one embodiment of the clinician programmer (CP) 60 (FIG. 1) that can be used to display the virtual reality representations discussed above. It is understood, however, that alternative embodiments of the CP may be used to perform these virtual reality representations as well.

The CP includes a printed circuit board ("PCB") that is populated with a plurality of electrical and electronic components that provide power, operational control, and protection to the CP. With reference to FIG. 17, the CP includes a processor 600. The processor 600 controls the CP. In one construction, the processor 600 is an applications processor model i.MX515 available from Freescale Semiconductor®. More specifically, the i.MX515 applications processor has internal instruction and data caches, multimedia capabilities, external memory interfacing, and interfacing flexibility. Further information regarding the i.MX515 applications processor can be found in, for example, the "IMX510EC, Rev. 4" data sheet dated August 2010 and published by Freescale Semiconductor® at www.freescale.com. The content of the data sheet is incorporated herein by reference. Of course, other processing units, such as other microprocessors, microcontrollers, digital signal processors, etc., can be used in place of the processor 600.

The CP includes memory, which can be internal to the processor 600 (e.g., memory 605), external to the processor 600 (e.g., memory 610), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The processor 600 executes software that is capable of being stored in the RAM (e.g., during execution), the ROM (e.g., on a generally permanent basis), or another non-transitory computer readable medium such as another memory or a disc. The CP also includes input/output ("I/O") systems that include routines for transferring information between components within the processor 600 and other components of the CP or external to the CP.

Software included in the implementation of the CP is stored in the memory 605 of the processor 600, RAM 610, ROM 615, or external to the CP. The software includes, for example, firmware, one or more applications, program data, one or more program modules, and other executable instructions. The processor 600 is configured to retrieve from memory and execute, among other things, instructions related to the control processes and methods described below for the CP.

One memory shown in FIG. 17 is memory 610, which may be a double data rate (DDR2) synchronous dynamic random access memory (SDRAM) for storing data relating to and captured during the operation of the CP. In addition, a secure digital (SD) multimedia card (MMC) may be coupled to the CP for transferring data from the CP to the memory card via slot 615. Of course, other types of data storage devices may be used in place of the data storage devices shown in FIG. 17.

The CP includes multiple bi-directional radio communication capabilities. Specific wireless portions included with the CP are a Medical Implant Communication Service (MICS) bi-directional radio communication portion 620, a WiFi bi-directional radio communication portion 625, and a Bluetooth bi-directional radio communication portion 630. The MICS portion 620 includes a MICS communication interface, an antenna switch, and a related antenna, all of which allows wireless communication using the MICS specification. The WiFi portion 625 and Bluetooth portion 630 include a WiFi communication interface, a Bluetooth communication interface, an antenna switch, and a related antenna all of which allows wireless communication following the WiFi Alliance standard and Bluetooth Special Interest Group standard. Of course, other wireless local area network (WLAN) standards and wireless personal area networks (WPAN) standards can be used with the CP.

The CP includes three hard buttons: a "home" button 635 for returning the CP to a home screen for the device, a "quick off" button 640 for quickly deactivating stimulation IPG, and a "reset" button 645 for rebooting the CP. The CP also includes an "ON/OFF" switch 650, which is part of the power generation and management block (discussed below).

The CP includes multiple communication portions for wired communication. Exemplary circuitry and ports for receiving a wired connector include a portion and related port for supporting universal serial bus (USB) connectivity 655, including a Type A port and a Micro-B port; a portion and related port for supporting Joint Test Action Group (JTAG) connectivity 660, and a portion and related port for supporting universal asynchronous receiver/transmitter (UART) connectivity 665. Of course, other wired communication standards and connectivity can be used with or in place of the types shown in FIG. 17.

Another device connectable to the CP, and therefore supported by the CP, is an external display. The connection to the external display can be made via a micro High-Definition Multimedia Interface (HDMI) 670, which provides a compact audio/video interface for transmitting uncompressed digital data to the external display. The use of the HDMI connection 670 allows the CP to transmit video (and audio) communication to an external display. This may be beneficial in situations where others (e.g., the surgeon) may want to view the information being viewed by the healthcare professional. The surgeon typically has no visual access to the CP in the operating room unless an external screen is provided. The HDMI connection 670 allows the surgeon to view information from the CP, thereby allowing greater communication between the clinician and the surgeon. For a specific example, the HDMI connection 670 can broadcast a high definition television signal that allows the surgeon to view the same information that is shown on the LCD (discussed below) of the CP.

The CP includes a touch screen I/O device 675 for providing a user interface with the clinician. The touch screen display 675 can be a liquid crystal display (LCD) having a resistive, capacitive, or similar touch-screen technology. It is envisioned that multitouch capabilities can be used with the touch screen display 675 depending on the type of technology used.

The CP includes a camera 680 allowing the device to take pictures or video. The resulting image files can be used to document a procedure or an aspect of the procedure. Other devices can be coupled to the CP to provide further information, such as scanners or RFID detection. Similarly, the CP includes an audio portion 685 having an audio codec circuit, audio power amplifier, and related speaker for providing audio communication to the user, such as the clinician or the surgeon.

The CP further includes a power generation and management block 690. The power block 690 has a power source (e.g., a lithium-ion battery) and a power supply for providing multiple power voltages to the processor, LCD touch screen, and peripherals.

In one embodiment, the CP is a handheld computing tablet with touch screen capabilities. The tablet is a portable personal computer with a touch screen, which is typically the primary input device. However, an external keyboard or mouse can be attached to the CP. The tablet allows for mobile functionality not associated with even typical laptop personal computers. The hardware may include a Graphical Processing Unit (GPU) in order to speed up the user experience. An Ethernet port (not shown in FIG. 17) may also be included for data transfer.

It is understood that a patient programmer may be implemented in a similar manner as the clinician programmer shown in FIG. 17. Also, according to the present disclosure, the virtual reality representation aspects discussed above with reference to FIGS. 2-16 may be implemented in an electronic device such as the clinician programmer 60 or a suitable patient programmer. For example, the virtual reality representations may be implemented on the clinician or patient programmers through an appropriate user interface, such as those shown in FIGS. 2-13 discussed above.

Furthermore, though the various virtual reality representation concepts of the present disclosure are explained using an implanted pulse generator (IPG) as an example, it is understood that these concepts may apply to other types of implanted medical devices as well, such as pacemakers, etc.

Figure 18A:
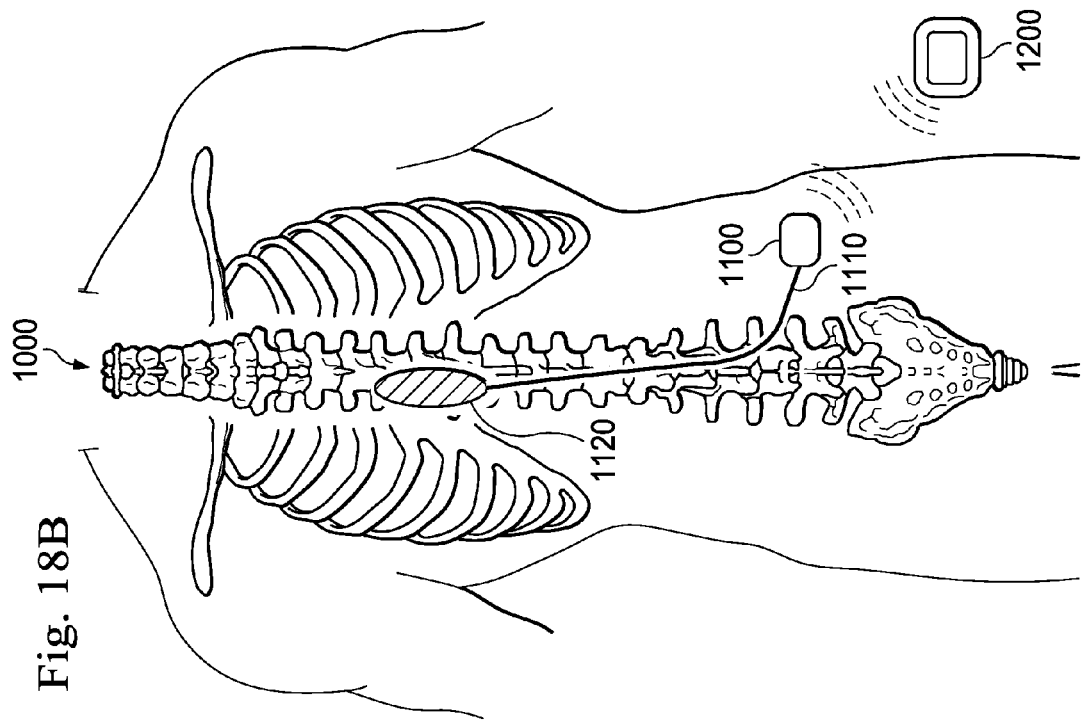
FIGS. 18A and 18B are side and posterior views of a human spine, respectively.
Figure 18B:
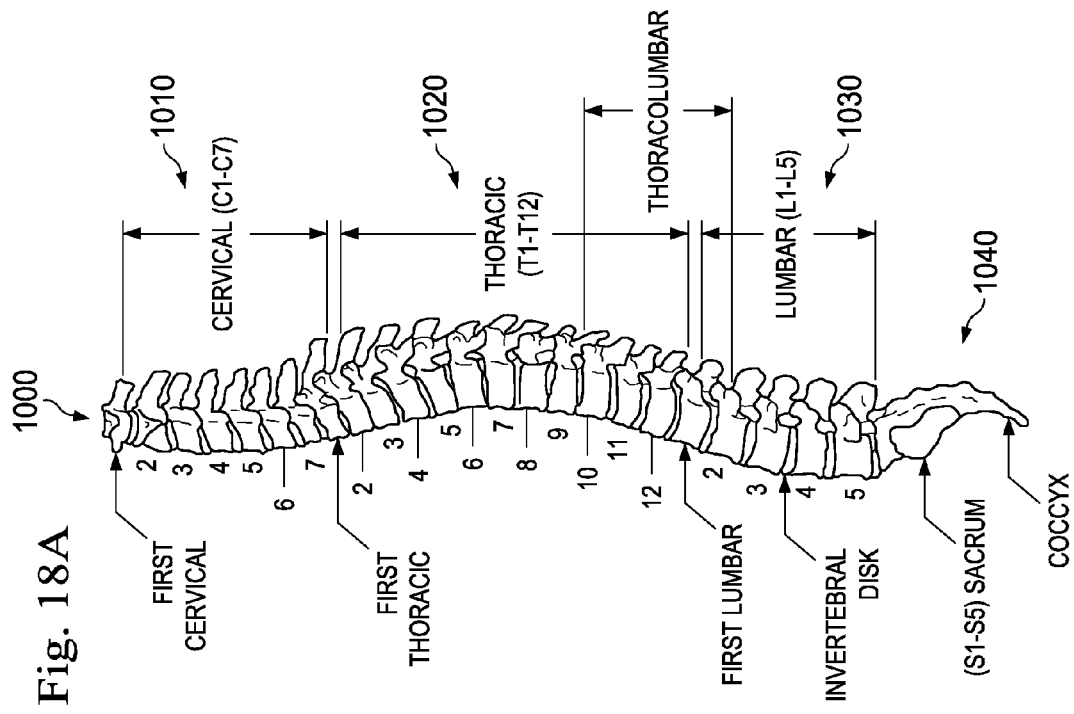

FIG. 18A is a side view of a spine 1000, and FIG. 18B is a posterior view of the spine 1000. The spine 1000 includes a cervical region 1010, a thoracic region 1020, a lumbar region 1030, and a sacrococcygeal region 1040. The cervical region 1010 includes the top 7 vertebrae, which may be designated with C1-C7. The thoracic region 1020 includes the next 12 vertebrae below the cervical region 1010, which may be designated with T1-T12. The lumbar region 1030 includes the final 5 "true" vertebrae, which may be designated with L1-L5. The sacrococcygeal region 1040 includes 9 fused vertebrae that make up the sacrum and the coccyx. The fused vertebrae of the sacrum may be designated with S1-S5.

Neural tissue (not illustrated for the sake of simplicity) branch off from the spinal cord through spaces between the vertebrae. The neural tissue can be individually and selectively stimulated in accordance with various aspects of the present disclosure. For example, referring to FIG. 18B, an IPG device 1100 is implanted inside the body. The IPG device 1100 may include a neurostimulator device. A conductive lead 1110 is electrically coupled to the circuitry inside the IPG device 1100. The conductive lead 1110 may be removably coupled to the IPG device 1100 through a connector, for example. A distal end of the conductive lead 1110 is attached to one or more electrodes 1120. The electrodes 1120 are implanted adjacent to a desired nerve tissue in the thoracic region 1020. Using well-established and known techniques in the art, the distal end of the lead 1110 with its accompanying electrodes may be positioned along or near the epidural space of the spinal cord. It is understood that although only one conductive lead 1110 is shown herein for the sake of simplicity, more than one conductive lead 1110 and corresponding electrodes 1120 may be implanted and connected to the IPG device 1100.

The electrodes 1120 deliver current drawn from the current sources in the IPG device 1100, therefore generating an electric field near the neural tissue. The electric field stimulates the neural tissue to accomplish its intended functions. For example, the neural stimulation may alleviate pain in an embodiment. In other embodiments, a stimulator may be placed in different locations throughout the body and may be programmed to address a variety of problems, including for example but without limitation; prevention or reduction of epileptic seizures, weight control or regulation of heart beats.

It is understood that the IPG device 1100, the lead 1110, and the electrodes 1120 may be implanted completely inside the body, may be positioned completely outside the body or may have only one or more components implanted within the body while other components remain outside the body. When they are implanted inside the body, the implant location may be adjusted (e.g., anywhere along the spine 1000) to deliver the intended therapeutic effects of spinal cord electrical stimulation in a desired region of the spine. Furthermore, it is understood that the IPG device 1100 may be controlled by a patient programmer or a clinician programmer 1200, the implementation of which may be similar to the clinician programmer shown in FIG. 17.

The foregoing has outlined features of several embodiments so that those skilled in the art may better understand the detailed description that follows. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. An electronic device configured to visualize one or more medical devices in its suitable anatomical surroundings, the electronic device comprising:
  a touchscreen display configured to receive input from a user and display an output to the user;
  a memory storage component configured to store programming code; and
  a computer processor configured to execute the programming code to perform the following tasks:
    illustrating, via the touchscreen display, a respective three-dimensional (3-D) model of a plurality of different kinds of medical devices that include at least a first medical device that comprises an implantable lead and a second medical device that comprises: an implantable pulse generator, an external pulse generator, or a connector block, wherein the respective 3-D model for each of the first medical device and the second medical device is configured to be moved and rotated in response to user input;
    illustrating, via the touchscreen display, a visual representation of a suitable anatomical surrounding for the first or second medical devices, wherein the visual representation of the anatomical surrounding is configured to be zoomed in and out and scaled up and down in response to user input;
    placing, in response to user input, the 3-D model of the first or second medical devices in a target position of the visual representation of the anatomical surrounding; and
    establishing a simulated coupling between the first medical device and the second medical device, wherein the establishing the simulated coupling comprises:

determining whether the simulated coupling causes a mismatch between the first medical device and the second medical device; and notifying the user that the simulated coupling is impermissible in response to a determination that the simulated coupling causes the mismatch between the first medical device and the second medical device.

2. The electronic device of claim 1, wherein the illustrating comprises illustrating the respective 3-D models of the plurality of different kinds of medical devices on a spinnable virtual carousel; and selecting, in response to user input, one of the medical devices from the virtual carousel to be further manipulated by the user.

3. The electronic device of claim 1, wherein the programming code can be executed to further perform the following tasks:

detecting, before the illustrating the respective 3-D models, a digital identification code in response to an image scan; and matching the detected digital identification code to a corresponding one of the plurality of different kinds of medical devices, wherein the corresponding one of the medical devices is one of the medical devices whose 3-D model is to be illustrated.

4. The electronic device of claim 3, wherein the digital identification code comprises one of: a barcode and a Quick Response (QR) code associated with the medical device, and wherein the digital identification code contains digital 3-D information of the medical device for rendering the 3-D model of the corresponding medical device on the touchscreen display of the electronic device.

5. The electronic device of claim 1, wherein the programming code can be executed to further perform the following task:

preventing inadvertent movement or rotation of the 3-D model of the first medical device or the second medical device; and removing the 3-D model of the first medical device or the second medical device from the touchscreen display.

6. The electronic device of claim 1, wherein the programming code can be executed to further perform the following task: configuring a relational pattern of the 3-D model of the first medical device.

7. The electronic device of claim 6, wherein the configuring a relational pattern comprises:

displaying a single lead pattern and a double lead pattern; and selecting, in response to user input, the single lead pattern or the double lead pattern as the implantable lead.

8. The electronic device of claim 1, wherein the programming code can be executed to further perform: communicating a failsafe message in response to a detection of one or more predefined events.

9. The electronic device of claim 1, wherein the electronic device is one of: a clinician programmer, a patient programmer, and a computer tablet, and wherein the electronic device is portable and is configured to communicate with external devices according to a wireless communications protocol.

10. The electronic device of claim 1, wherein the tasks further comprise: visually emphasizing, via the touchscreen display, at least one of the first and second medical devices in response to a successful simulated coupling between the first and second medical devices.

11. A medical system, comprising:

one or more medical devices configurable to deliver a medical therapy to a patient; and an electronic device configured to provide a visual representation of the one or more medical devices via a touch-sensitive visual user interface, wherein the electronic device includes a non-transitory, tangible machine-readable storage medium storing a computer application, wherein the computer application contains machine-readable instructions that when executed electronically by processors, perform the following actions:

demonstrating, via a spinnable virtual carousel in the touch-sensitive visual user interface, three-dimensional models of an implantable lead as a first medical device and at least one of: an implantable pulse generator, an external pulse generator, or a connector block as a second medical device;

demonstrating, via the touch-sensitive visual user interface, a virtual reality representation of a suitable anatomical environment for at least one of the first and second medical devices;

positioning the at least one of the first and second medical devices in a target area of the anatomical environment;

simulating an electrical or physical coupling between the first and second medical devices in response to user input, wherein the simulating comprises:

determining whether the simulated electrical or physical coupling causes a mismatch between the first medical device and the second medical device; and notifying a user that the simulated electrical or physical coupling is impermissible in response to a determination that the simulated electrical or physical coupling causes the mismatch between the first medical device and the second medical device.

12. The medical system of claim 11, wherein:

the virtual reality representations of the first and second medical devices comprise three-dimensional models that are movable, rotatable, lockable, and removable; and the virtual reality representation of the suitable anatomical environment is zoomable and scalable.

13. The medical system of claim 11, wherein the electronic device further comprises an integrated camera, and wherein the instructions are executed by processors to further perform:

scanning a digital code with the integrated camera; and displaying, via the touch-sensitive visual user interface, a virtual reality representation of a medical device associated with the digital code.

14. The medical system of claim 11, wherein the instructions are executed by processors to further perform: setting a relational pattern of the virtual reality representation of at least one of the first and second medical devices.

15. The medical system of claim 14, wherein the setting the relational pattern comprises:

displaying a single lead pattern and a double lead pattern; and setting, in response to user input, the single lead pattern or the double lead pattern as the implantable lead.

16. The medical system of claim 11, wherein the instructions are executed by processors to further perform: communicating a failsafe warning in response to a detection of one or more predefined events.

17. The medical system of claim 11, wherein the electronic device has a portable form factor and comprises a wireless transceiver.

18. The medical system of claim 11, wherein:
the first medical device comprises: the implantable lead;
the second medical device comprises the implantable pulse generator, an external pulse generator, or a connector block; and
the electronic device comprises: one of: a clinician programmer, a patient programmer, and a computer tablet.

19. The medical system of claim 11, wherein the tasks further comprise: visually emphasizing, via the touch-sensitive visual user interface, at least one of the first and second medical devices in response to a successful simulated coupling between the first and second medical devices.

20. A method of facilitating visualization of devices in a medical context, comprising:
displaying, via a touch-sensitive user interface, a virtual reality representation of at least a first medical device comprising an implantable lead and a second medical device comprising: an implantable pulse generator, an external pulse generator, or a connector block, wherein the virtual reality representation of the first and second medical devices includes a movable and rotatable three-dimensional model for each of the first and second medical devices;
displaying, via the touch-sensitive user interface, a virtual reality representation of an anatomical environment of a patient, wherein the virtual reality representation of the anatomical environment is zoomable and scalable;
customizing the virtual reality representation of the first or the second medical device; and
positioning the customized virtual reality representation of the first or the second medical device in an target location of the virtual reality representation of the anatomical environment;
establishing a simulated coupling between the first medical device and the second medical device, wherein the establishing the simulated coupling comprises:
determining whether the simulated coupling causes a mismatch between the first medical device and the second medical device; and
notifying a user that the simulated coupling is impermissible in response to a determination that the simulated coupling causes the mismatch between the first medical device and the second medical device;
wherein the customizing and the positioning are performed in response to user input.

21. The method of claim 20, wherein the displaying the virtual reality representation of the medical device comprises:
offering virtual reality representations of a plurality of different types of medical devices on a spinnable digital carousel, the different types of medical devices including the first and second medical devices; and
selecting, in response to user input, one of the medical devices from the digital carousel to be customized.

22. The method of claim 20, further comprising, before the displaying of the virtual reality representation:
detecting a digital identifier in response to an image scan; and
matching the digital identifier to a corresponding medical device, wherein the corresponding medical device is one of the medical devices whose virtual reality representation is to be displayed.

23. The method of claim 22, wherein the digital identifier comprises one of: a barcode and a Quick Response (QR) code associated with the medical device.

24. The method of claim 20, wherein the three-dimensional model of the medical device is lockable and deletable.

25. The method of claim 20, wherein the customizing comprises setting a relational pattern of the virtual reality representation of the first medical device.

26. The method of claim 25, wherein the setting the relational pattern comprises:
displaying a single lead pattern and a double lead pattern; and
setting, in response to user input, the single lead pattern or the double lead pattern as the implantable lead.

27. The method of claim 20, further comprising: communicating a failsafe message in response to a detection of one or more predefined events.

28. The method of claim 20, wherein the touch-sensitive user interface is displayed on a touch-sensitive screen of a portable electronic device with wireless communication capabilities.

29. The method of claim 28, wherein the portable electronic device comprises one of: a clinician programmer, a patient programmer, and a computer tablet.

30. The method of claim 20, further comprising: visually emphasizing, via the touch-sensitive user interface, at least one of the first and second medical devices in response to a successful simulated coupling between the first and second medical devices.

31. An electronic apparatus for displaying virtual reality representations of medical devices, the electronic apparatus comprising:
user interface means for communicating with a user, the user interface means including a touch-sensitive screen;
memory storage means for storing executable instructions; and
computer processor means for executing the instructions to perform:
displaying, via the touch-sensitive screen, a virtual representation of a portion of a human body;
displaying, via the touch-sensitive screen, a virtual carousel containing a plurality of three-dimensional (3-D) models corresponding to a plurality of different types of medical devices that include at least a first medical device and a second medical device, respectively, wherein the first medical device comprises an implantable pulse generator, and wherein the second medical device comprises: an implantable pulse generator, an external pulse generator, or a connector block; and
placing, in response to user input received through the user interface means, the 3-D models of one or more of the medical devices within an appropriate location of the virtual representation of the portion of the human body; and
establishing a simulated coupling between the first medical device and the second medical device, wherein the establishing the simulated coupling comprises:
determining whether the simulated coupling causes a mismatch between the first medical device and the second medical device; and
notifying the user that the simulated coupling is impermissible in response to a determination that the simulated coupling causes the mismatch between the first medical device and the second medical device.

32. The electronic apparatus of claim 31, wherein the computer processor executes the instructions to further perform: customizing the 3-D models of the different types of the medical devices.

33. The electronic apparatus of claim 32, wherein the customizing the 3-D models comprises configuring a relational pattern of the different types of the medical devices.

34. The electronic apparatus of claim 33, wherein the configuring the relational pattern comprises:
displaying a single lead pattern and a double lead pattern; and
setting, in response to user input, the single lead pattern or the double lead pattern as the implantable lead.

35. The electronic apparatus of claim 31, further comprising, imaging means for capturing a digital identifier associated with a medical tool; and wherein the computer processor executes the instructions to further perform: displaying, via the touch-sensitive screen, a 3-D model of the medical tool associated with the digital identifier.

36. The electronic apparatus of claim 35, wherein the digital identifier comprises one of: a barcode and a Quick Response (QR) code located on a packaging of the medical tool.

37. The electronic apparatus of claim 31, wherein the virtual representation of the portion of the human body is zoomable and scalable.

38. The electronic apparatus of claim 31, wherein the 3-D models of the medical devices are rotatable, movable, lockable, and removable.

39. The electronic apparatus of claim 31, wherein the computer processor means is configured to execute the instructions to further perform: visually emphasizing, via the touch-sensitive screen, at least one of the first and second medical devices in response to a successful simulated coupling between the first and second medical devices.

40. The electronic apparatus of claim 31, wherein the computer processor executes the instructions to further perform: communicating a failsafe message in response to a detection of a predefined event.

* * * * *